United States Patent
Sheikh et al.

(10) Patent No.: US 8,348,664 B2
(45) Date of Patent: Jan. 8, 2013

(54) ORTHODONTIC DEVICE AND METHOD FOR TREATING MALOCCLUSIONS

(75) Inventors: Hamid Sheikh, Chino, CA (US);
Dwight Damon, Spokane, WA (US);
Kevin Corcoran, Corona, CA (US)

(73) Assignee: Ormco Corporation, Orange, CA (US)

( * ) Notice: Subject to any disclaimer, the term of this patent is extended or adjusted under 35 U.S.C. 154(b) by 0 days.

(21) Appl. No.: 12/540,423

(22) Filed: Aug. 13, 2009

(65) Prior Publication Data

US 2009/0291405 A1    Nov. 26, 2009

Related U.S. Application Data

(62) Division of application No. 11/621,813, filed on Jan. 10, 2007, now Pat. No. 7,578,672.

(60) Provisional application No. 60/757,944, filed on Jan. 11, 2006.

(51) Int. Cl.
*A61C 3/00* (2006.01)

(52) U.S. Cl. .......................................... 433/19; 433/18

(58) Field of Classification Search .................. 433/6–7, 433/18–24, 215, 140
See application file for complete search history.

(56) References Cited

U.S. PATENT DOCUMENTS

| | | | |
|---|---|---|---|
| 3,618,214 A | 11/1971 | Armstrong | |
| 3,798,773 A | 3/1974 | Northcutt | |
| 4,462,800 A | 7/1984 | Jones | |
| 4,618,324 A | 10/1986 | Nord | |
| 4,795,342 A | 1/1989 | Jones | |
| 5,011,404 A | 4/1991 | Losi | |
| 5,120,218 A | 6/1992 | Hanson | |
| 5,183,388 A | 2/1993 | Kumar | |
| 5,352,116 A | 10/1994 | West | |
| 5,378,147 A | 1/1995 | Mihailowitsch | |
| 5,545,037 A | 8/1996 | Takeshi | |
| 5,562,445 A | 10/1996 | DeVincenzo et al. | |

(Continued)

FOREIGN PATENT DOCUMENTS

DE    201 16 895    12/2001

(Continued)

OTHER PUBLICATIONS

Laure Acquaviva (Authorized Officer); Partial Search Report for PCT/US2007/000618; Aug. 2, 2007; 2 pages; European Patent Office.

(Continued)

*Primary Examiner* — Yogesh Patel
(74) *Attorney, Agent, or Firm* — Wood, Herron & Evans, LLP

(57) ABSTRACT

A dental apparatus for use with a connecting member coupled to a jaw in a patient's mouth. The apparatus includes an orthodontic device and a connecting device carried by the orthodontic device. The connecting device includes a receptacle adapted to partially receive the connecting member and a blocking member. The blocking member is moveable relative to the receptacle between an opened position in which the connecting member may be disengaged from the receptacle and a closed position in which the connecting member is captured within the receptacle for pivotally engaging the orthodontic device with the connecting member. The orthodontic device may further include a biasing member selectively activated to provide a spring-biased force to the jaw. A method of using the dental apparatus includes moving the blocking member to capture/release the connecting member in the receptacle and activating/deactivating the biasing member to operate the apparatus in a different mode.

18 Claims, 17 Drawing Sheets

U.S. PATENT DOCUMENTS

| | | | |
|---|---|---|---|
| 5,620,321 A | 4/1997 | Thornburg et al. | |
| 5,632,618 A | 5/1997 | Jensen | |
| 5,678,990 A | 10/1997 | Rosenberg | |
| 5,711,667 A | 1/1998 | Vogt | |
| 5,738,514 A | 4/1998 | DeVincenzo et al. | |
| 5,829,975 A | 11/1998 | Gold | |
| 5,919,042 A | 7/1999 | Williams | |
| 5,944,518 A | 8/1999 | Sabbagh | |
| 5,964,588 A | 10/1999 | Cleary | |
| 5,976,774 A | 11/1999 | Uchihiro | |
| 5,980,247 A | 11/1999 | Cleary | |
| 6,012,920 A | 1/2000 | Woo | |
| 6,036,488 A | 3/2000 | Williams | |
| 6,053,730 A | 4/2000 | Cleary | |
| 6,113,390 A | 9/2000 | Sirney et al. | |
| 6,162,051 A | 12/2000 | Brehm et al. | |
| 6,168,430 B1 | 1/2001 | Higgins | |
| 6,234,792 B1 | 5/2001 | DeVincenzo | |
| 6,241,517 B1 | 6/2001 | Williams | |
| 6,290,495 B1 | 9/2001 | Jabri | |
| 6,322,357 B1 | 11/2001 | Vogt | |
| 6,328,562 B1 | 12/2001 | Sirney et al. | |
| 6,358,046 B1 * | 3/2002 | Brehm et al. | 433/19 |
| 6,361,315 B1 | 3/2002 | Hanks | |
| 6,402,510 B1 | 6/2002 | Williams | |
| 6,413,082 B2 | 7/2002 | Binder | |
| 6,520,722 B2 | 2/2003 | Hopper et al. | |
| 6,547,560 B1 | 4/2003 | Vazquez | |
| 6,558,160 B2 | 5/2003 | Schnaitter et al. | |
| 6,589,051 B2 | 7/2003 | Cleary | |
| 6,655,959 B2 | 12/2003 | Farzin-Nia et al. | |
| 6,669,474 B2 | 12/2003 | Vogt | |
| 6,702,575 B2 | 3/2004 | Hilliard | |
| 6,719,557 B1 | 4/2004 | Williams | |
| 6,769,910 B1 | 8/2004 | Pantino | |
| 6,877,982 B2 | 4/2005 | Williams | |
| 6,913,460 B2 | 7/2005 | Cleary et al. | |
| 6,964,566 B2 | 11/2005 | Sapian | |
| 6,976,839 B2 | 12/2005 | Lluch | |
| 6,988,888 B2 | 1/2006 | Cleary | |
| 2002/0025501 A1 | 2/2002 | Clark | |
| 2002/0025502 A1 | 2/2002 | Williams | |
| 2002/0031741 A1 | 3/2002 | Williams | |
| 2002/0164555 A1 | 11/2002 | Vogt | |
| 2002/0172909 A1 * | 11/2002 | Williams | 433/19 |
| 2003/0022124 A1 | 1/2003 | Schnaitter et al. | |
| 2003/0022125 A1 | 1/2003 | Cleary | |
| 2003/0091952 A1 * | 5/2003 | Bowman et al. | 433/18 |
| 2003/0157455 A1 | 8/2003 | Taramoto | |
| 2003/0207226 A1 | 11/2003 | Forster | |
| 2003/0232301 A1 | 12/2003 | Cleary et al. | |
| 2004/0219474 A1 * | 11/2004 | Cleary | 433/19 |
| 2005/0260533 A1 | 11/2005 | Lluch | |

FOREIGN PATENT DOCUMENTS

| | | |
|---|---|---|
| JP | S61047098 | 10/1986 |
| JP | S62006456 | 2/1987 |
| JP | H08509644 | 10/1996 |
| JP | H11019099 | 1/1999 |
| JP | 2002-512074 | 4/2002 |
| JP | 2005506127 | 3/2005 |
| WO | 9426198 | 11/1994 |
| WO | 9953858 | 10/1999 |
| WO | 03032859 | 4/2003 |
| WO | 2004103200 | 12/2004 |

OTHER PUBLICATIONS

Claudio Salvatore; International Search Report and Written Opinion for PCT/US2007/000618; Aug. 31, 2007; 13 pages; European Patent Office.

Claudio Salvatore; International Preliminary Report on Patentabiity for PCT/US2007/000618; May 19, 2008; 10 pages; European Patent Office.

Japanese Patent Office, Office Action for application 2009-288193, mailed Nov. 1, 2011; 6 pp. including English translation.

Japanese Patent Office, Office Action for application 2008-550376, mailed Nov. 1, 2011; 6 pp. including English translation.

* cited by examiner

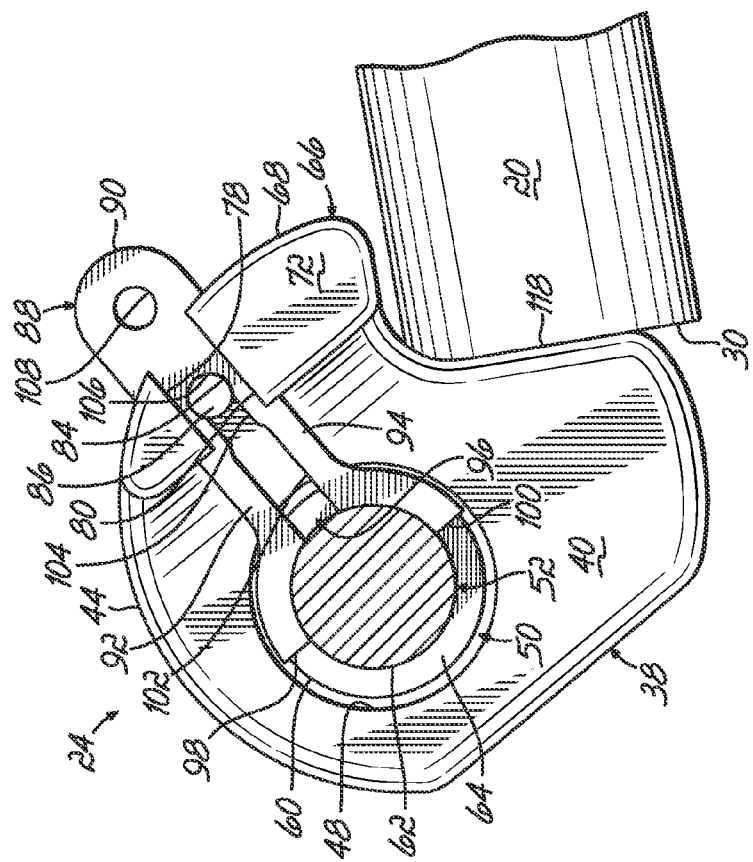
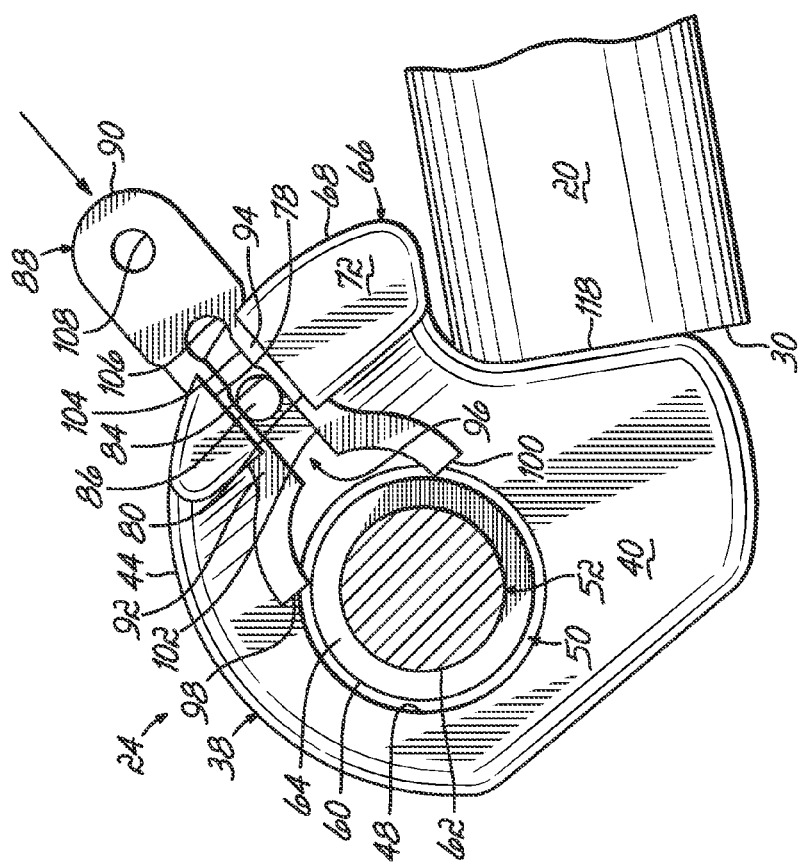
FIG. 5B
FIG. 5A

ORTHODONTIC DEVICE AND METHOD FOR TREATING MALOCCLUSIONS

CROSS REFERENCE TO RELATED APPLICATION

This application is a divisional of U.S. patent application Ser. No. 11/621,813, filed on Jan. 10, 2007, now U.S. Pat. No. 7,578,672, which claims the benefit of U.S. patent application Ser. No. 60/757,944, filed Jan. 11, 2006, the entire disclosures of which are incorporated herein by reference.

FIELD OF THE INVENTION

The present invention relates generally to orthodontic appliances, and more particularly to an orthodontic device and methods for treating malocclusions.

BACKGROUND OF THE INVENTION

Orthodontic treatment involves movement of malpositioned teeth to orthodontically correct positions. During treatment, small orthodontic appliances known as brackets are often coupled to anterior, bicuspid, and molar teeth, and an archwire is placed in a slot of each bracket. The archwire forms a track to guide movement of the brackets and the associated teeth to desired positions for correct occlusion. Typically, the ends of the archwire are held by appliances known as buccal tubes that are secured to a patient's molar teeth. The brackets, archwires, and buccal tubes are commonly referred to as "braces."

The orthodontic treatment of some patients also includes correcting the alignment of the upper dental arch, or maxillary jaw, and the lower dental arch, or mandibular jaw. For example, certain patients have a condition referred to as a Class II malocclusion, or "overbite," where the lower dental arch is located an excessive distance in a rearward direction relative to the location of the upper dental arch when the jaws are closed. Other patients may have an opposite condition referred to as a Class III malocclusion, or "underbite," wherein the lower dental arch is located in a forward direction of its desired location relative to the position of the upper dental arch when the jaws are closed.

Class II and Class III malocclusions are commonly corrected by movement of the lower dental arch relative to the upper dental arch. In order to minimize the overall length of time by which a patient must undergo orthodontic treatment, it is typically desirable to achieve this correction at the same time that archwires and brackets are used to move individual teeth to desired positions. For example, oftentimes the movement of the lower dental arch is achieved by applying forces to brackets, buccal tubes, archwires, or attachments connected to these orthodontic appliances.

A number of orthodontic appliances for treating malocclusions have been developed. One of the most popular of such orthodontic appliances is commonly referred to as a "Herbst" device. A conventional Herbst device is comprised of a telescoping sleeve and rod assembly. Typically, one component of the assembly is pivotally secured to a molar tooth in the upper arch, while the other component is pivotally secured to a bicuspid or anterior tooth in the lower arch (or a cantilever arm in the lower arch). Oftentimes both the sleeve and rod components are pivotally secured to their respective dental arches using a screw that is inserted through an opening or eyelet in the respective components and coupled to a threaded member on the archwire, bracket, cap or other orthodontic appliance.

Herbst devices operate by forcing the lower arch into a desired occlusion position when the mouth is closed. In other words, the Herbst device prevents a patient from comfortably closing his or her mouth unless the arches are physically repositioned for proper occlusion. If the arches are not properly repositioned, the sleeve of the Herbst device impacts an end portion of the rod so as to create a hard, fixed "stop" that is uncomfortable for the patient. To compensate for this uncomfortable stop the patient repositions their mandibular jaw forward. Eventually, the patient experiences physiological adaptation based upon a learned response such that the jaws begin to naturally close with the proper occlusion. As treatment progresses, spacers may be positioned on the rod to properly reposition the hard, fixed stop once the jaws have begun to adapt, thereby permitting continued treatment and further adaptation of the jaws to the proper occlusion.

While Herbst devices are generally successful for moving the jaws over a significant distance and in a relatively short period of time, it is sometimes necessary to follow treatment using a Herbst device with treatment using a spring-biased bite corrector. For instance, it is not uncommon for the jaws to slightly relapse out of proper occlusion after treatment with a Herbst device. In these cases, the relapse is often corrected using a spring-biased bite corrector. To this end, the Herbst device is typically removed from the teeth and mouth of the patient and a separate spring-biased bite corrector is installed on the teeth.

Spring-biased bite correctors may be arranged to generate a push-type force to move the mandibular jaw or teeth forward and typically include a spring or flexible member that applies a biasing force on the mandibular jaw or teeth to achieve movement. The spring is biased when the jaws are closed such that it applies a force generally along the normal growth direction for a human jaw. The connection between a spring-biased bite corrector and the upper and lower arches is typically complex, utilizing multiple separate parts. For instance, the posterior end of the bite corrector is typically coupled to a buccal tube on an upper molar using a bayonet wire or pin which has a first end coupled to the posterior of the bite corrector and a free end that is first threaded through the buccal tube and then bent back on itself thereby coupling the posterior end to the upper arch. The anterior end of the bite corrector typically includes an eyelet, which is positioned on, and moves freely along, the archwire on the lower arch. Alternately, the anterior end of the bite corrector may be positioned on an auxiliary wire associated with the lower arch.

In addition to the above, spring-biased bite correctors may also be used in other orthodontic treatments. For example, if the malocclusion is relatively small, therefore not generally requiring significant muscular and skeletal adaptation, a spring-biased bite corrector may be used in the first instance to correct the malocclusion. Spring-biased bite correctors may also be used in the orthodontic treatment of adult patients where physiological adaptation to the jaw may be more limited.

In any event, there are some drawbacks to the current orthodontic devices for the treatment of malocclusions as described above. The different approaches and devices for treating a malocclusion, i.e., Herbst device or spring-biased bite corrector, requires a physician to store multiple devices having multiple, separate parts, which increases the size and complexity of inventory. Providing multiple devices also requires the doctor and staff to be trained for and become familiar with each of the devices. In addition, when a physician desires to switch treatment between a Herbst device and a spring-biased bite corrector, or vice versa, the physician typically physically removes one device from the mouth of the patient and then installs the other, separate device on the teeth. This can be a time consuming and therefore a costly process.

In addition to the above, another drawback is that connections that pivotally couple the Herbst device or the spring-biased bite corrector to the upper and lower arches require assembling multiple separate pieces, which may be difficult and time consuming. This may be particularly true if the device is coupled to a molar in the posterior of the mouth and therefore having limited accessibility. Moreover, in order to maintain the pivotal connection and withstand the forces exerted during orthodontic treatment, the connectors that couple the device to the teeth, as well as the tools used to make the connection, are often large and bulky. These components and associated tools may therefore cause patient discomfort through contact with oral tissues. In yet another drawback, current connectors, and especially screw-based connectors, provide very limited movement of the jaws in a lateral direction (i.e., left to right movements). This leads to increased device breakage, as patients attempt to move their jaws in the lateral direction, and is generally uncomfortable for the patient.

Accordingly, there is a need in the orthodontic art for improved devices and methods of treating malocclusions that address these and other drawbacks of current orthodontic devices.

SUMMARY OF THE INVENTION

Embodiments of the invention are directed to a dental apparatus for use with a connecting member that is coupled to a jaw of a patient's mouth. The apparatus includes an orthodontic device and a connecting device carried by the orthodontic device. The connecting device includes a receptacle adapted to partially receive the connecting member and a blocking member movable relative to the receptacle between an opened position and a closed position. In the opened position, the connecting member may be disengaged from the receptacle; and in the closed position, the connecting member is captured within the receptacle so as to pivotally engage the orthodontic device with the connecting member.

In one embodiment, the orthodontic device includes a Class II corrector having a first member and a second tubular member having a first end and a second end, which carries the connecting device. The first member is insertable into the first end of the tubular second member for telescoping relative movement of the first and second members. The first member may also carry a connecting device. The blocking member may include first and second legs that extend about a narrow portion of the connecting member when the blocking member is in the closed position to secure a wide portion of the connecting member between the receptacle and the blocking member. A pin may be positioned between the first and second legs and have an interference fit with the first and second legs to inhibit movement of the blocking member from the closed position to the opened position.

Alternately, the blocking member may include a spring clip having a portion that extends about a narrow portion of the connecting member when the blocking member is in the closed position to secure a wide portion of the connecting member between the receptacle and the blocking member. The spring clip is resiliently biased to inhibit movement of the blocking member from the closed position to the opened position. In another embodiment, the blocking member may include a rotatable drum having a cutout portion that communicates with a central aperture therein. The cutout portion of the drum aligns with a bore in the connecting device when in the opened position to provide a pathway for inserting the connecting member in the receptacle. When the drum is in the closed position, the cutout portion is misaligned with the bore in the connecting device to at least partially capture the connecting member in the receptacle. The connecting device may include a detent and the drum may include a spring element, wherein the detent and spring element cooperate so as to inhibit movement of the blocking member from the closed position to the opened position.

In another embodiment of the invention, a convertible orthodontic device for connecting the mandibular jaw with the maxillary jaw includes a tubular first member and a second member telescopically received within the first member to define a tubular space. The first and second members are arranged for relative movement as the mandibular jaw moves relative to the maxillary jaw. A biasing member may be positioned in the tubular space. The orthodontic device also includes a spacer capable of being positioned on the second member wherein the spacer is adapted to cause the biasing member to exert a biasing force opposing relative movement of the first and second members when the spacer is positioned on the second member.

In one embodiment, the biasing member may be a compression spring having coils capable of being compressed during at least a portion of the relative telescoping movement of the first and second members. In another embodiment, the spacer may be configured as a tubular sleeve dimensioned to fit within the tubular space so as to abut the compression spring and compress the coils. In another embodiment, the spacer may be configured as a crimpable stop capable of being crimped to the second member so as to abut the compression spring and compress the coils.

A method of using an orthodontic device in accordance with the invention includes securing inner and outer telescoping member of an orthodontic device, such as a Class II orthodontic device, between the mandibular jaw and maxillary jaw, operating the inner and outer telescoping member of the orthodontic device in a Herbst operating mode to reposition the mandibular jaw relative to the maxillary jaw, and activating a biasing member carried by the telescoping members of the orthodontic device to convert the orthodontic device from the Herbst operating mode to a second operating mode in which the active biasing member applies a biasing force directed to reposition the mandibular jaw relative to the maxillary jaw. The second operating mode may be a spring-biased mode or a mixed operating mode utilizing aspects of both the Herbst mode and spring-biased mode.

In yet another embodiment, a method for mounting an orthodontic device to a connecting member coupled to a patient's jaw includes partially inserting a connecting member into a receptacle of a connecting device carried by the orthodontic device and moving a blocking member carried by the connecting device relative to the receptacle to capture the connecting member within the receptacle and thereby pivotally engage the orthodontic device with the connecting member.

These and other objects, advantages and features of the invention will become more readily apparent to those of ordinary skill in the art upon review of the following detailed description taken in conjunction with the accompanying drawings.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the principles of the invention.

FIG. 5A is a rear view of the lower connecting device of the orthodontic device shown in FIG. 4 with the blocking member in the opened position;

FIG. 5B is a view of the lower connecting device shown in FIG. 5A with the blocking member in the closed position;

DETAILED DESCRIPTION

Figure 1:
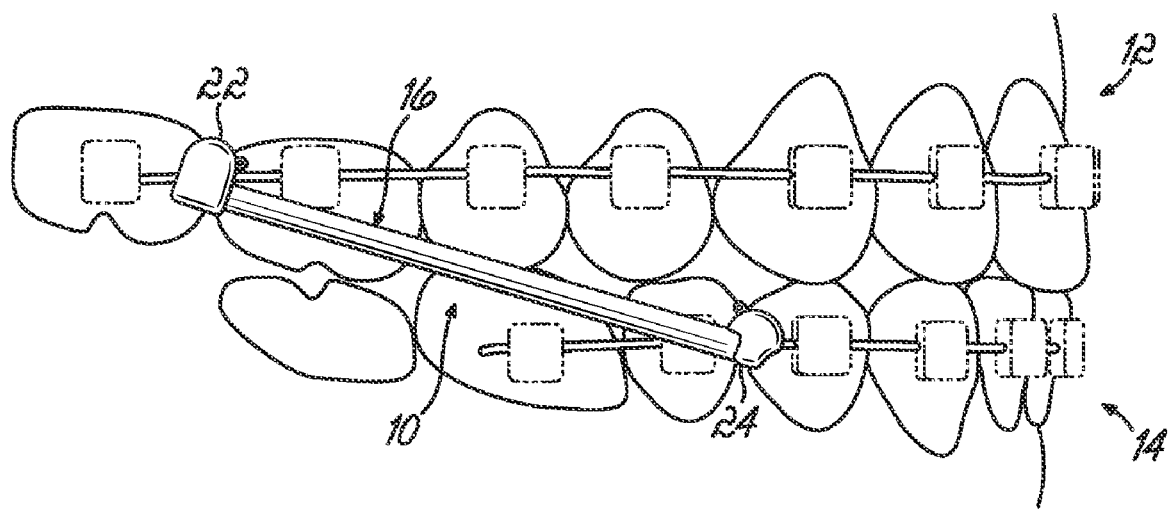
FIG. 1 is a schematic diagram showing an embodiment of the orthodontic device in accordance with the invention installed in the mouth of a patient and with the jaws in a closed position.
Figure 2:
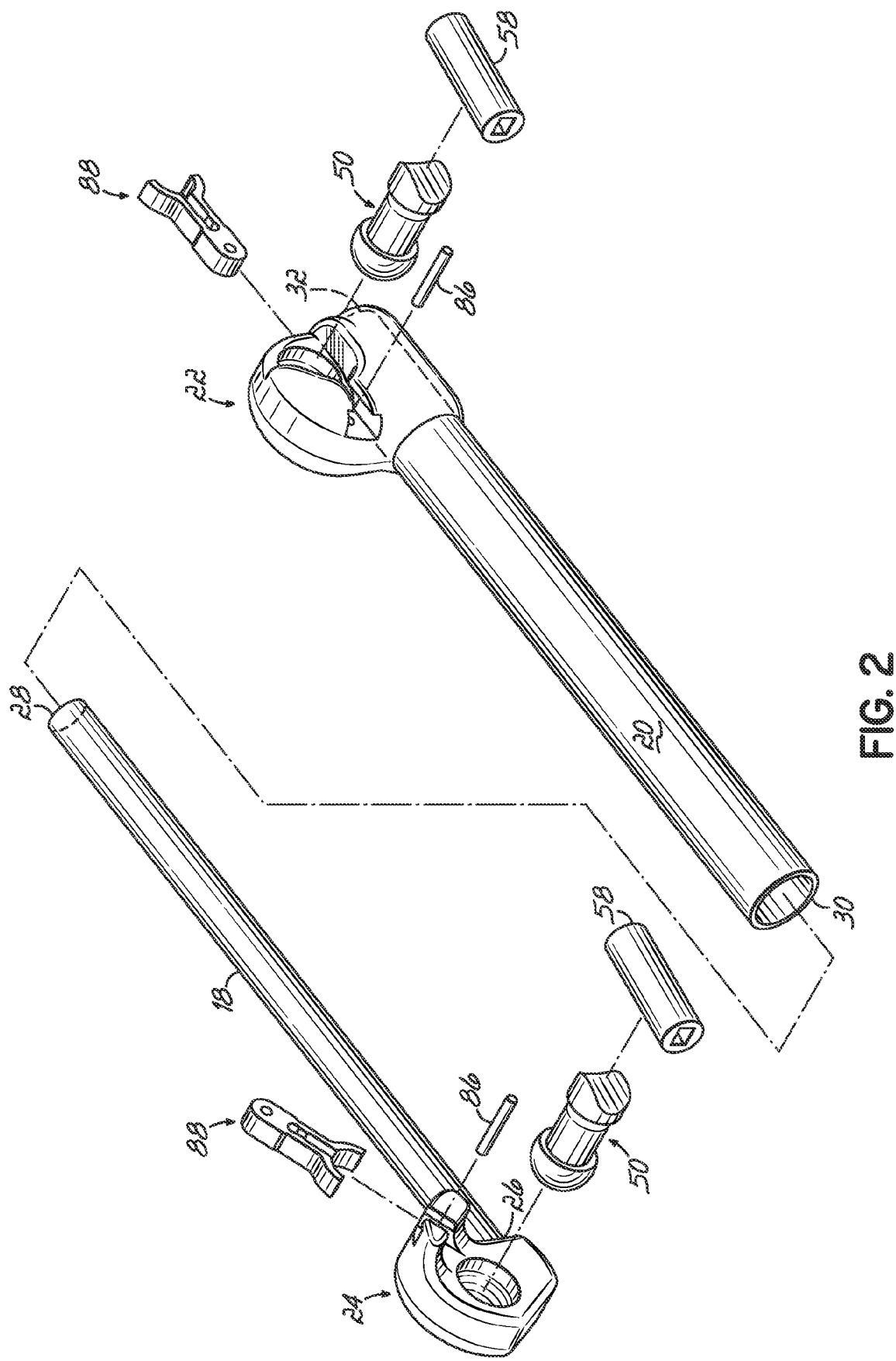
FIG. 2 is a disassembled perspective view of an embodiment of the orthodontic device in accordance with the invention.
Figure 3:
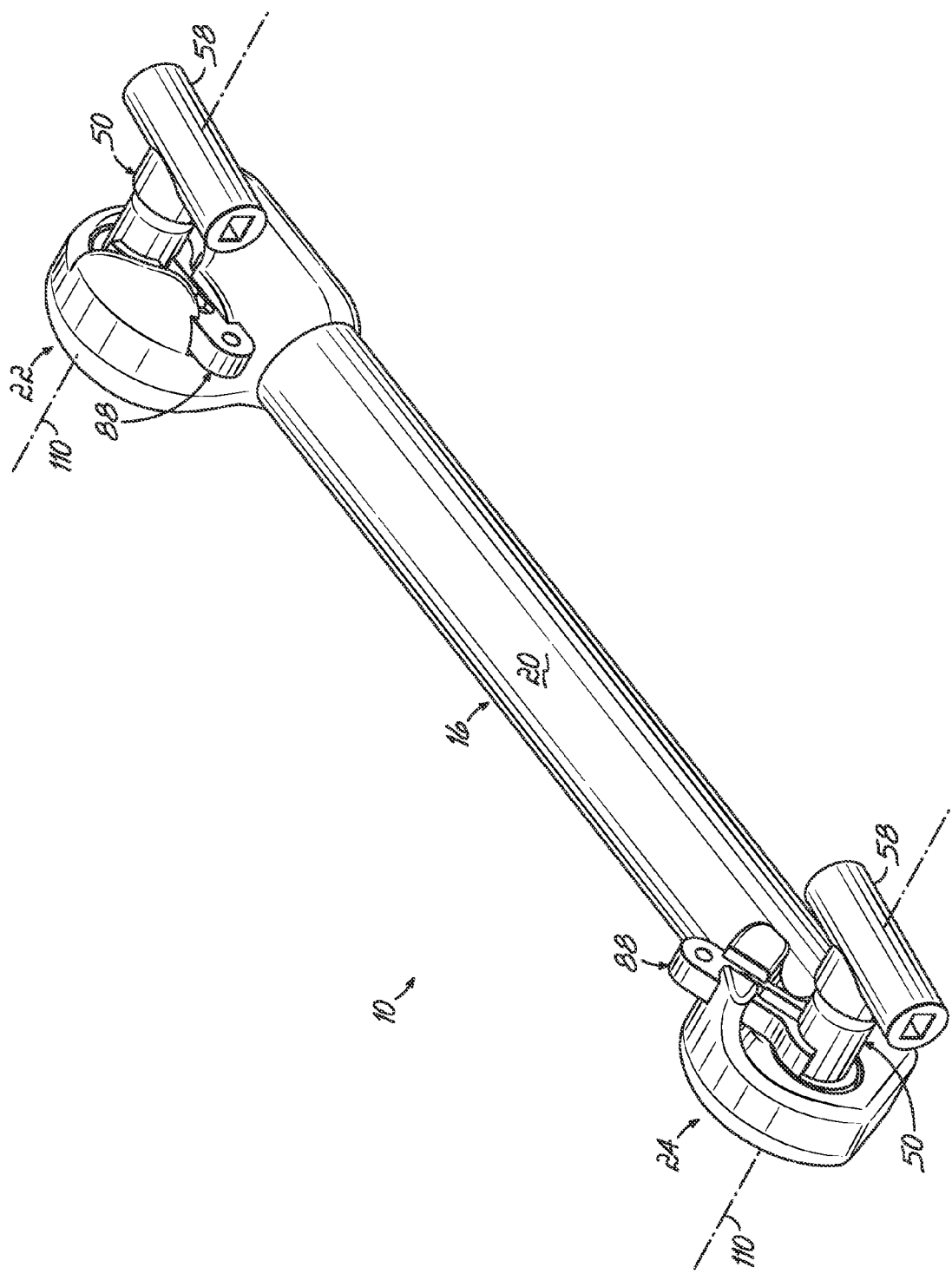
FIG. 3 is an assembled perspective view of the orthodontic device shown in FIG. 2.
Figure 4:
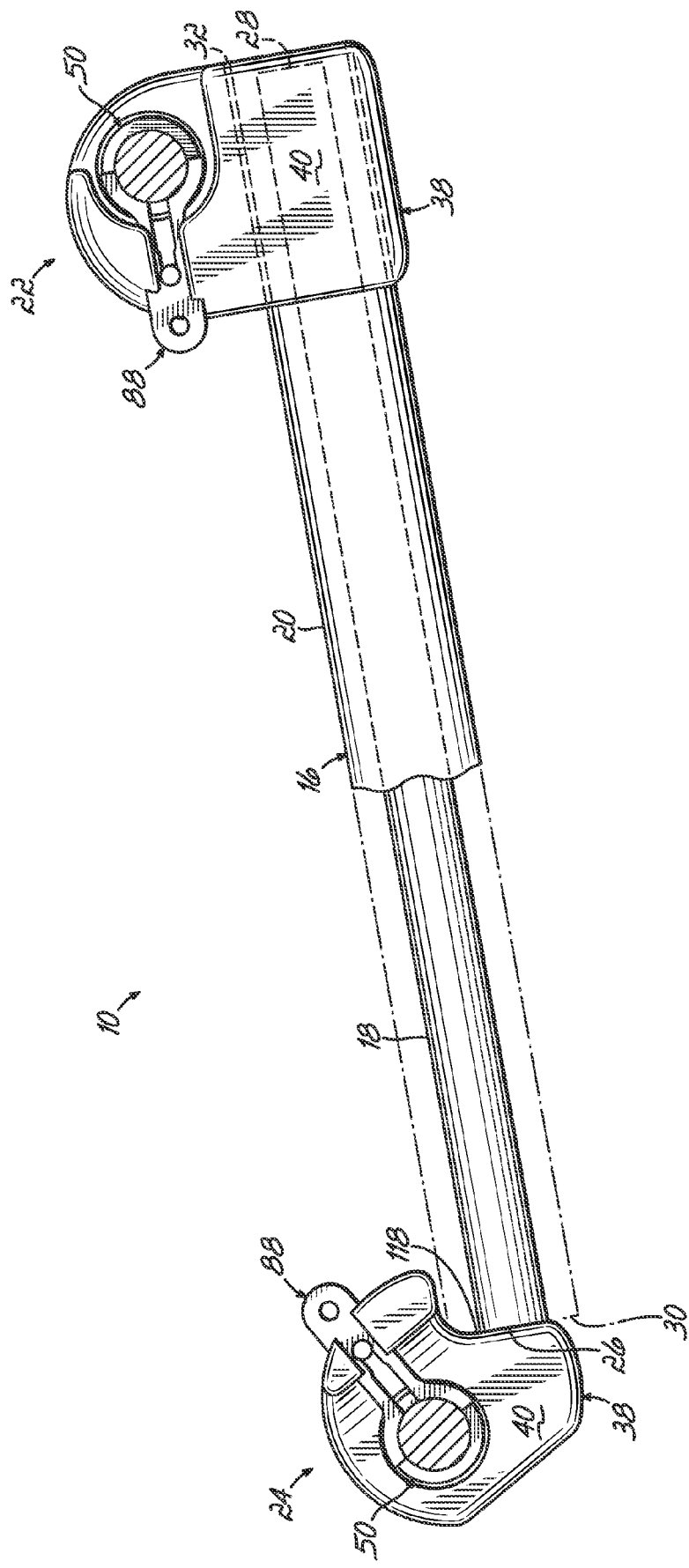
FIG. 4 is a rear, partially torn away view of the orthodontic device shown in FIG. 3.

Referring to FIGS. 1-4, an orthodontic device 10 according to one embodiment of the invention may be coupled to the upper dental arch, or maxillary jaw 12, and the lower dental arch, or mandibular jaw 14, so as to reposition the mandibular jaw 14 relative to the maxillary jaw 12 and therefore correct a malocclusion, such as a Class II malocclusion. The orthodontic device 10 includes a telescoping rod assembly 16, comprising an inner rod 18 and an outer sleeve 20, and upper and lower connecting devices 22, 24, respectively.

The inner rod 18 includes a first end 26 and a second opposed end 28. The first end 26 of inner rod 18 is coupled to the lower connecting device 24. In a similar manner, outer sleeve 20 includes a first end 30 and a second opposed end 32. The second end 32 of the outer sleeve 20 is coupled to the upper connecting device 22. The inner rod 18 is configured to fit within the outer sleeve 20 to provide the telescoping feature of the assembly 16. To this end, the second end 28 of inner rod 18 may be inserted into the outer sleeve 20 via the first end 30 of the outer sleeve 20. In one embodiment, the second end 28 of the inner rod 18 may include a taper to facilitate insertion of the inner rod 18 into the outer sleeve 20. Although the inner rod 18 is shown as a solid member, the inner rod 18 may alternately be configured as a tubular member.

As shown in FIG. 1, the upper connecting device 22 may be coupled to the maxillary jaw 12, and the lower connecting device 24 may be coupled to the mandibular jaw 14 toward the anterior of the mouth. The telescoping rod assembly 16 allows the orthodontic device 10 to expand and contract as the jaws 12, 14 open and close. Such an arrangement enables the orthodontic device 10 to facilitate the correction of malocclusions, as will be described in greater detail below.

Figure 6:
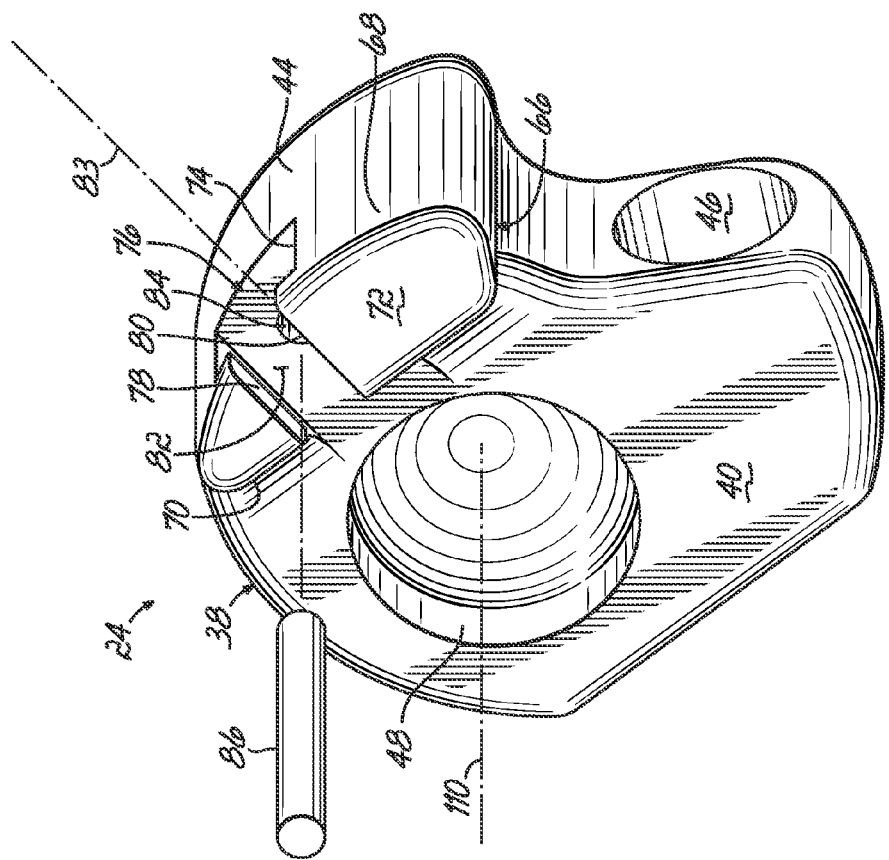
FIG. 6 is a perspective, partially disassembled view of the lower connecting device shown in FIG. 5A with the blocking member removed for clarity.
Figure 5C:
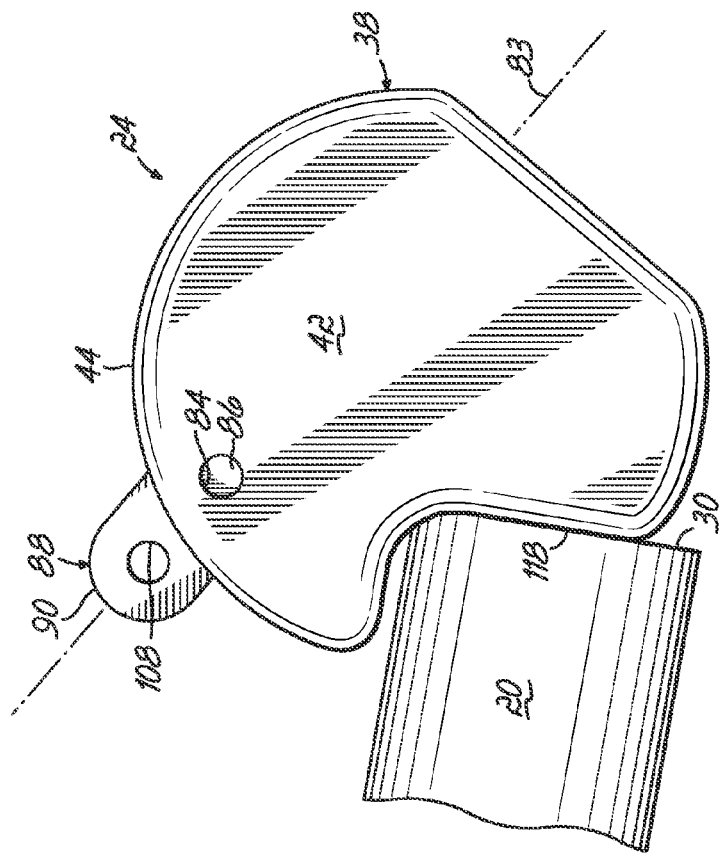
FIG. 5C is a front view of the lower connecting device shown in FIG. 5A.
Figure 7:
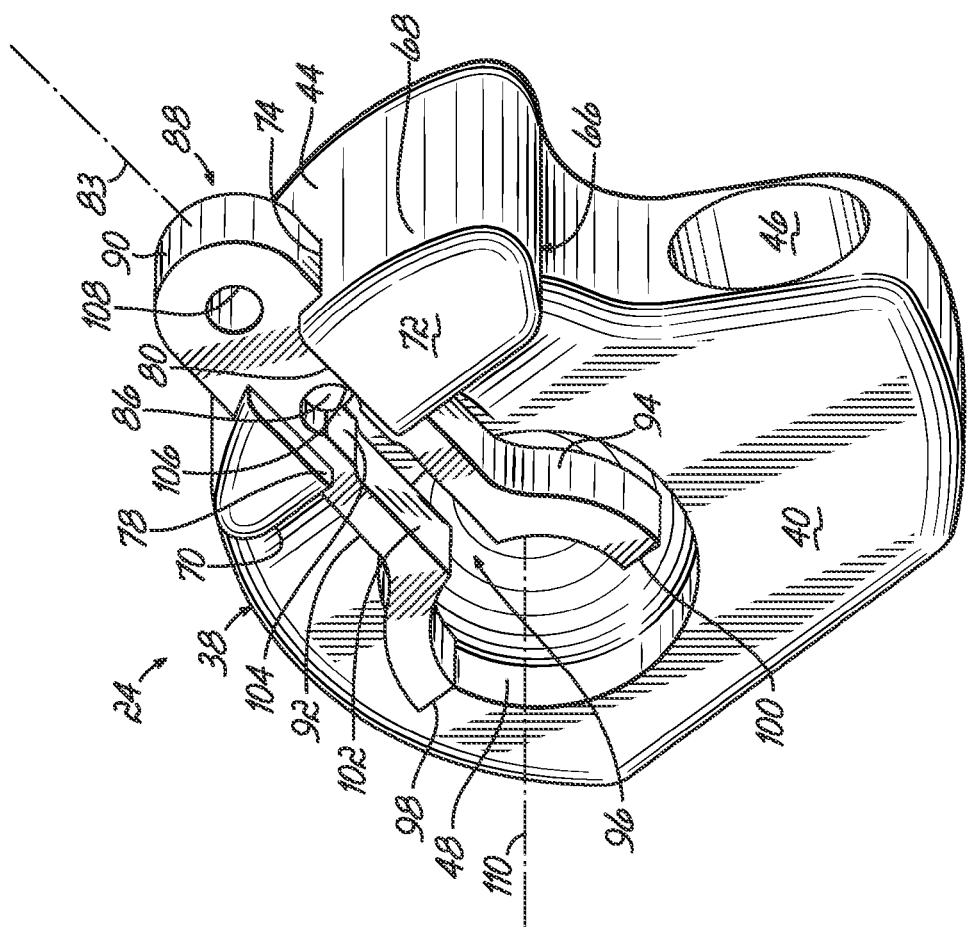
FIG. 7 is a view of the lower connecting device shown in FIG. 6 with the blocking member shown.

In one aspect of the invention, the orthodontic device 10 may be coupled to the maxillary and mandibular jaws 12, 14 in an improved manner. Specifically, upper and lower connecting devices 22, 24 may be configured as a unitary assembly, devoid of screws, bayonet pins, auxiliary wires or other detached parts, which may be selectively coupled to or removed from the upper and lower dental arches in a quick and convenient manner. To this end, and as shown in FIGS. 5A-5C, lower connecting device 24 includes a body portion 38 having a tooth-facing surface 40, a buccal surface 42 and a side surface 44 connecting surfaces 40, 42. Side surface 44 includes a bore 46 (FIGS. 6 and 7) adapted to receive the first end 26 of the inner rod 18. As shown in FIG. 5C, buccal surface 42 may be configured to be a smooth, uninterrupted surface having gentle and rounded edges. Such a configuration prevents soft tissue impingement resulting in greater patient comfort.

Figure 8:
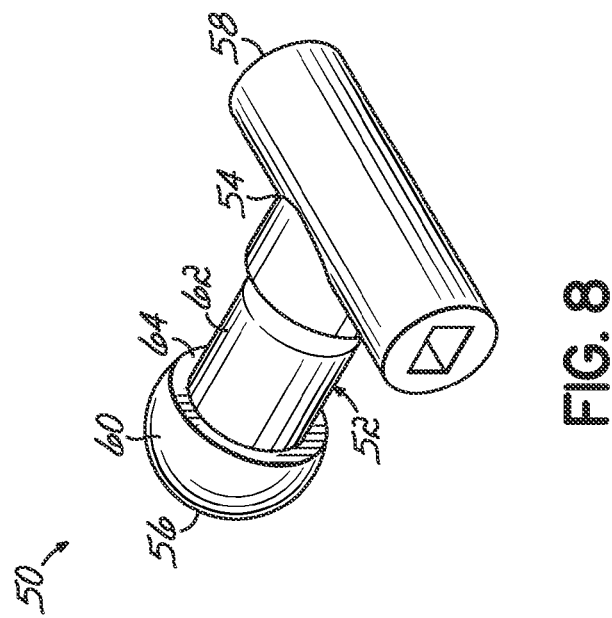
FIG. 8 is a perspective view of an embodiment of a connecting member in accordance with the invention.

As shown in FIGS. 5A, 5B, 6 and 7, the tooth-facing surface 40 of lower connecting device 24 includes a receptacle 48. The receptacle 48 is adapted to cooperate with a connecting member 50 to couple the orthodontic device 10 to the mandibular jaw 14. In one embodiment, and as shown in FIG. 8, the connecting member 50 may be configured as a rod or stem 52 having a first end 54 and a second end 56. The first end 54 of stem 52 is adapted to be coupled to the mandibular jaw 14. For instance, the first end 54 may be coupled to an archwire, buccal tube, bracket, crown, band, cantilever arm or other orthodontic appliances associated with the mandibular jaw 14. In one embodiment, the first end 54 of stem 52 may be coupled to a tube member 58, which in turn may be coupled with an archwire associated with the mandibular jaw 14. The tube member 58 may be coupled to stem 52 by any suitable method, such as welding, for example, or may be integrally formed therewith. The invention is not so limited, however, as those of ordinary skill in the art will recognize other ways to couple the first end 54 of stem 52 with the mandibular jaw 14, such as through welding or brazing.

The second end 56 of stem 52 may be configured as a ball portion 60 that is enlarged relative to the stem 52 to define a neck portion 62 and a shoulder 64. The ball portion 60 of stem 52 is adapted to be received in receptacle 48 of connecting device 24 and secured thereto in a manner that will now be described.

As shown in FIGS. 5A, 5B, 6 and 7, connecting device 24 includes an extension portion 66 that projects from tooth-facing surface 40 and includes an outer surface 68 that is flush with side surface 44, an inner surface 70 and an end surface 72 connecting outer and inner surfaces 68, 70. A T-shaped opening 74 is formed in projecting portion 66 and extends from outer surface 68 to inner surface 70 and intersects end surface 72. Opening 74 defines a slot 76 and a pair of opposed ears 78, 80 that at least partially enclose slot 76. Slot 76 extends along an axis 83 which intersects the receptacle 48 in tooth-facing surface 40. An interior wall 82 of slot 76, opposite ears 78, 80, includes a bore 84 adapted to receive a dowel pin 86. When the dowel pin 86 is positioned in bore 84, a portion of pin 86 projects into slot 76. The function of dowel pin 86 will described in more detail below.

As shown in FIGS. 5A, 5B, 7 and 9, connecting device 24 further includes a blocking member, represented by yoke 88, that is configured to be received and retained in slot 76 and cooperate with slot 76 to allow movement of yoke 88 along axis 83. To this end, yoke 88 includes an end portion 90 and two opposed legs 92, 94. Legs 92, 94 define a slot 96 therebetween, which receives dowel pin 86 when the yoke 88 is positioned in slot 76. The yoke 88 is at least partially retained in slot 76 by ears 78, 80. The terminating ends 98, 100 of legs 92, 94 are arcuately shaped and project outwardly or away from the opposed leg.

Slot 96 includes a first portion 102, an intermediate portion 104 and a closed end portion 106. The width of slot 96 along first portion 102 is slightly larger than a cross dimension, e.g. diameter, of dowel pin 86 so as to allow yoke 88 to move along axis 83 with limited resistance. When the dowel pin 86 is positioned along first portion 102, terminating ends 98, 100 are moved away from receptacle 48 (FIG. 5A). This is referred to herein as an opened position. As the yoke 88 is moved toward receptacle 48 along axis 83, the dowel pin 86 engages intermediate portion 104. Intermediate portion 104 is narrowed relative to first portion 102 to have a width smaller than the cross dimension of dowel pin 86. This provides a snug, interference fit between the yoke 88 and dowel pin 86 that limits movement of yoke 88 along axis 83. The closed end portion 106 is shaped similar to dowel pin 86 and receives dowel pin 86 in a snap-fit manner as the yoke 88 is moved towards receptacle 48 (FIG. 5B). When dowel pin 86 is positioned in closed end portion 106, the terminating ends 98, 100 of legs 92, 94 overlie receptacle 48. This is referred to herein as a closed position. When in the closed position, yoke 88 may only move relative to slot 76 and in a direction away from receptacle 48 by application of a sufficient force to overcome the resistance provided by the dowel pin 86 traversing intermediate portion 104. To this end, end portion 90 may include an aperture 108 for engaging a tool (not shown) that facilitates movement of the yoke 88 between the opened and closed positions.

The yoke 88 and receptacle 48 of connecting device 24 cooperate to couple connecting device 24 to connecting member 50, which, as mentioned above, is coupled to the mandibular jaw 14. To this end, and with reference to FIGS. 5A and 5B, yoke 88 may be moved to the opened position so that yoke 88 is moved away from receptacle 48. The connecting device 24 may then be positioned over connecting member 50 such that ball portion 60 is received in receptacle 48 as connecting device 24 is moved toward the teeth. Once the ball portion 60 is located in receptacle 48, the yoke 88 is moved to its closed position by applying a sufficient force to overcome the resistance of the dowel pin 86 along intermediate portion 104 and position dowel pin 86 in closed end portion 106. As shown in FIG. 5B, when in the closed position, the arcuate terminating ends 98, 100 of legs 92, 94 snugly engage the neck portion 62 of stem 52 and connecting device 24 is securely coupled to connecting member 50.

In an advantageous aspect, the ball and socket configuration, as well as the manner in which the yoke 88 engages the stem 52, as described above, prevents undesired movement of connecting device 24 away from connecting member 50 along an axis 110, yet permits rotation of connecting member 50, and thus orthodontic device 10, around axis 110. When the connecting device 24 is coupled to connecting member 50, any movement of connecting device 24 away from connecting member 50 would cause shoulder 64 to contact an inner edge of yoke 88 thereby preventing any further movement. Moreover, the interaction of ball portion 60 with receptacle 48 and the interaction of the terminating ends 98, 100 with neck portion 62 do not inhibit rotation of connecting device 24 relative to connecting member 50 about axis 110. Furthermore, the ball and socket configuration permits increased lateral movement relative to previous connections.

In yet another advantageous aspect, connecting device 24 may be selectively coupled to or removed from connecting member 50 by movement of yoke 88 between the opened and closed position. This allows the orthodontic device 10 to be installed and removed from the teeth in a quick and convenient manner without the drawbacks of screws or other separable parts or without the use of bulky tools.

Those of ordinary skill in the art will recognize that while the description above is directed to lower connecting device 24, upper connecting device 22 may be constructed in a similar manner and operate in a similar manner. Accordingly, the description above for lower connecting device 24 also applies to upper connecting device 22. Additionally, a connecting member similar to the connecting member 50 used to couple lower connecting device 24 to the mandibular jaw 14 may also be used to couple the upper connecting device 22 to the maxillary jaw 12. Any modifications between the upper and lower connecting devices 22, 24 for operation of the orthodontic device 10 are readily recognized by those of ordinary skill in the art. Those of ordinary skill in the art will further recognize that the connecting devices 22, 24 as described above are not limited to the orthodontic device 10 described herein, but may be used in a wide variety of orthodontic devices where a connection between the device and the upper and/or lower arches is desired. For example, the connecting devices 22, 24 may be used with the Herbst device disclosed in U.S. patent application Ser. Nos. 60/702,142 and 11/459,530, the disclosures of which are incorporated by reference herein in their entirety.

The installation of the orthodontic device 10 will now be described. Connecting members 50 are positioned on the maxillary jaw 12 and mandibular jaw 14 in their desired positions and in a manner previously discussed. The yokes 88 on the upper and lower connecting devices 22, 24 are moved to their opened positions. The lower connecting device 24 is moved so that ball portion 60 on lower connecting member 50 is received in receptacle 48. The yoke 88 is then moved to a closed position to securely couple the lower connecting device 24 to the mandibular jaw 14. The upper connecting device 22 is likewise moved so that ball portion 60 on upper connecting member 50 is received in receptacle 48 of upper connecting device 22. The yoke 88 is then moved to the closed position to securely couple the upper connecting device 22 to the maxillary jaw 12. As those of ordinary skill in the art will recognize, the upper connecting device 22 may be coupled to the maxillary jaw 12 prior to the coupling of the lower connecting device 24 to the mandibular jaw 14. Also note that the removal of the orthodontic device 10 may be achieved by essentially performing the steps described above in a reverse order. In other words, the yokes 88 on the upper and lower connecting devices 22, 24 may be moved to the opened position and the connecting devices 22, 24 moved away from their corresponding connecting members 50 to remove the orthodontic device 10 from the patient's mouth Because the repetition of installation and removal at different times during treatment can lead to wear on the various components, the most inexpensive and easily-replaceable components should be designed to experience wear first. For example, the dowel pin 86 and intermediate portion 104 of yoke 88 are likely to experience wear during repeated installation and removal due to the interference between the parts. Although a variety of materials may be used to construct these components, in one embodiment the yoke 88 may be constructed from 440 stainless steel and the dowel pin 86 constructed from nickel titanium (NiTi). Such a combination helps ensure that the dowel pin 86, which can be easily produced and replaced, experiences wear from the interference rather than the yoke 88.

Figure 11:
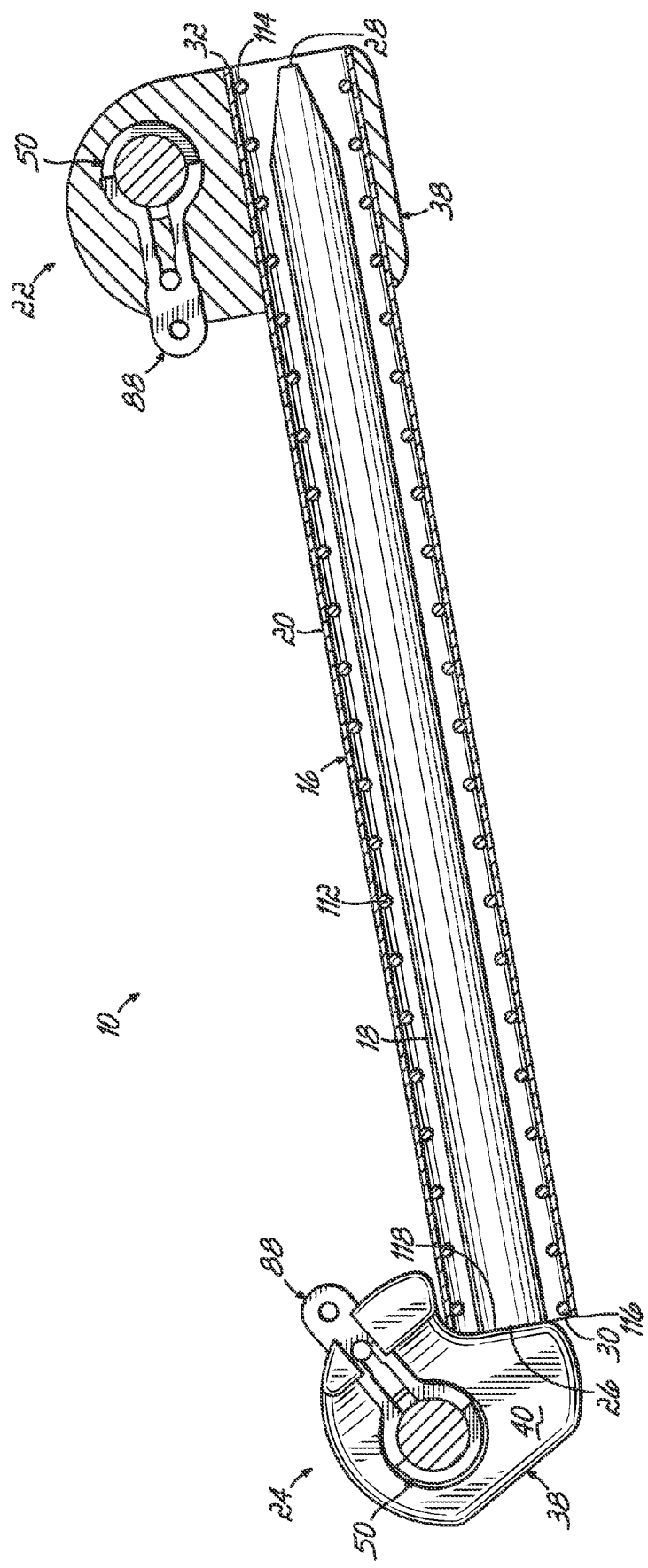
FIG. 11 is a cross-sectional view of an orthodontic device in accordance with an embodiment of the invention.

In yet another advantageous aspect, the orthodontic device 10 may be a convertible orthodontic device capable of being selectively operated in a plurality of treatment modes. Thus, for example, a single device may function as a Herbst device and as a spring-biased bite corrector. To this end and as shown in FIG. 11, orthodontic device 10 may include a biasing member, represented by spring 112, that is disposed within a space between the inner rod 18 and the outer sleeve 20. For instance, the spring 112 may be associated with the outer sleeve 20 and have a diameter that is substantially equal to the inner diameter of the outer sleeve 20, though the invention is not so limited. A first end 114 of the spring 112 may be coupled to the upper connecting device 22 (not shown) or alternately be coupled to the second end 32 of outer sleeve 20. This effectively fixes the position of the first end 114 of spring 112 relative to outer sleeve 20. Those of ordinary skill in the art will recognize other ways to fix the first end 114 of spring 112 and be within the scope of the invention.

The spring 112 extends along outer sleeve 20 and terminates at a second end 116. Depending on the particular application, the second end 116 may extend beyond outer sleeve 20, be substantially equal to outer sleeve 20 or may be located intermediate the first and second ends 30, 32 of outer sleeve 20. The spring 112 may be configured such that it does not apply a force to the mandibular jaw 14 (Herbst mode). Spring 112 may also be selectively activated, to apply a force to mandibular jaw 14 (spring-biased mode). The orthodontic device 10 may also be configured to operate in a mixed mode utilizing both Herbst and spring-biased corrections.

Operation of the convertible orthodontic device 10 in a Herbst mode will now be described. When the orthodontic device 10 is installed on the maxillary and mandibular jaws 12, 14 and in a closed position (FIG. 1), the inner rod 18 is substantially positioned within outer sleeve 20. Moreover, the first end 30 of outer sleeve 20 abuts and engages a contact portion 118 of lower connecting device 24. In this mode of operation, the second end 116 of spring 112 is not compressed (i.e., moved toward first end 114) and therefore no biasing force is applied to the maxillary jaw 14 via the spring 112. The interaction between the first end 30 of outer sleeve 20 and contact portion 118 provides the hard, fixed stop used in traditional Herbst devices. If a patient attempts to move the mandibular jaw 14 in a rearward direction when the jaws 12, 14 are closed, the outer sleeve 20 will exert a force against the lower connecting device 24 to counteract this attempted movement.

The pivotal relationship between the connecting devices 22, 24 and the respective connecting members 50, along with the slidable nature of the telescoping rod assembly 16, enable the patient to move his or her jaws 12, 14 into an opened position. In other words, when the jaws 12, 14 are open and the connecting devices 22, 24 are moved further apart from each other, a portion of the inner rod 18 slides out of the outer sleeve 20 along an axis formed between the connecting devices 22, 24 thereby allowing further expansion of the jaws 12, 14. Such an arrangement ensures that the orthodontic device 10 does not significantly interfere with chewing, speaking, yawning, and other movements that require expansion of the maxillary and mandibular jaws 12, 14.

When the patient attempts to close his or her jaws 12, 14, the outer sleeve 20 slides over the inner rod 18 until the first end 30 of outer sleeve 20 contacts the contact portion 118 of lower connecting device 24. If the mandibular jaw 14 is positioned an excessive distance in a rearward direction relative to the location of the maxillary jaw 12, the orthodontic device 10 will be angled relative to its normal position and prevent the jaws 12, 14 from completely closing. Thus, in order to move the maxillary and mandibular jaws 12, 14 into a closed position, the patient must force the mandibular jaw 14 in a forward direction until the orthodontic device 10 becomes aligned with its initial position. As with conventional Herbst devices, eventually the patient will experience muscular and/or skeletal adaptation based upon this forced response and begin closing his or her jaws 12, 14 with the proper occlusion.

Figure 10A:
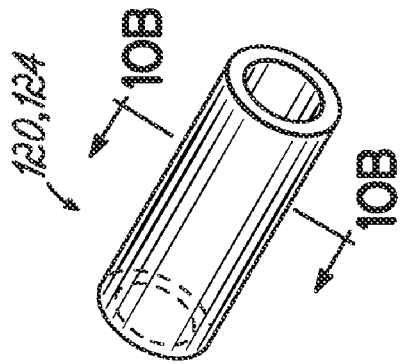
FIG. 10A is a perspective view of a spacer used in embodiments of the invention.
Figure 10B:
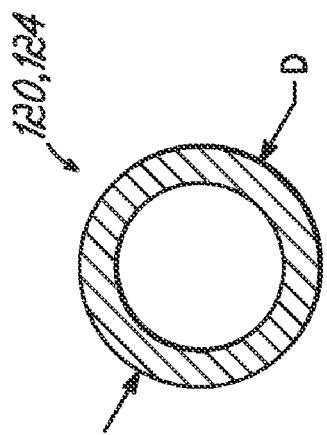
FIG. 10B is a cross-sectional view of the spacer shown in FIG. 10A.
Figure 9:
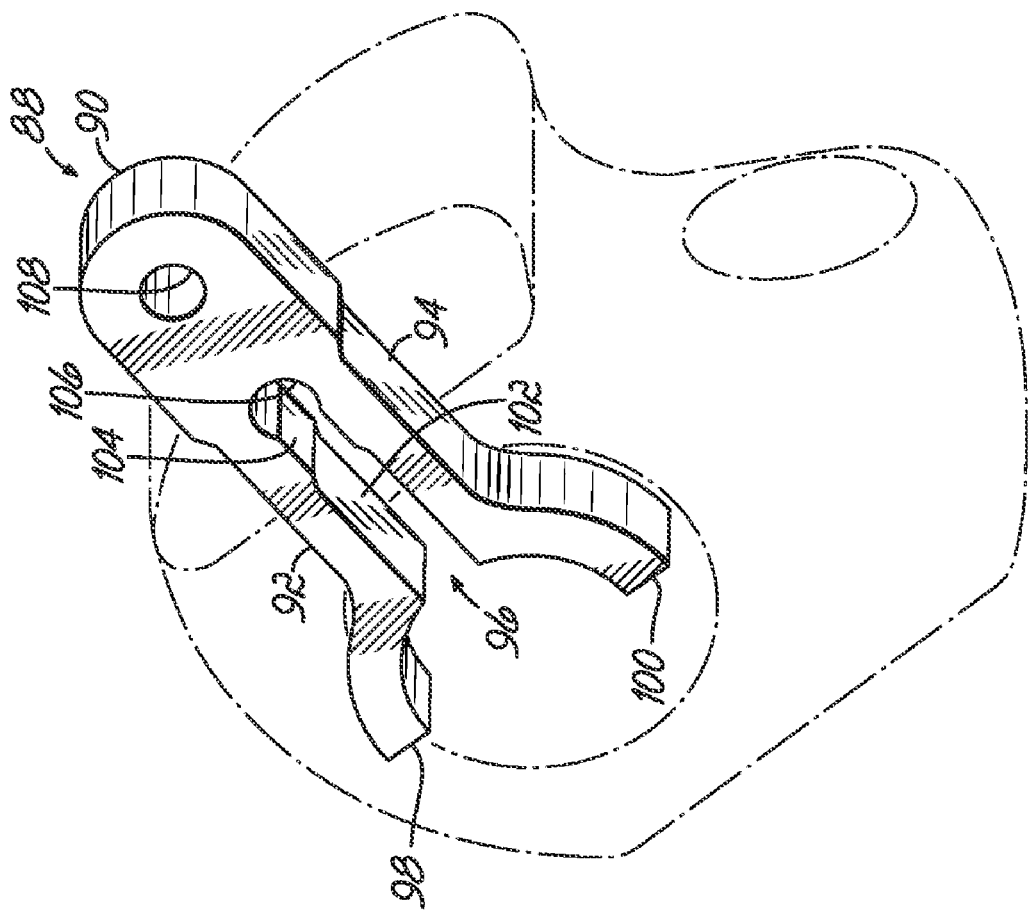
FIG. 9 is a perspective view of an embodiment of the blocking member configured as a yoke.
Figure 12:
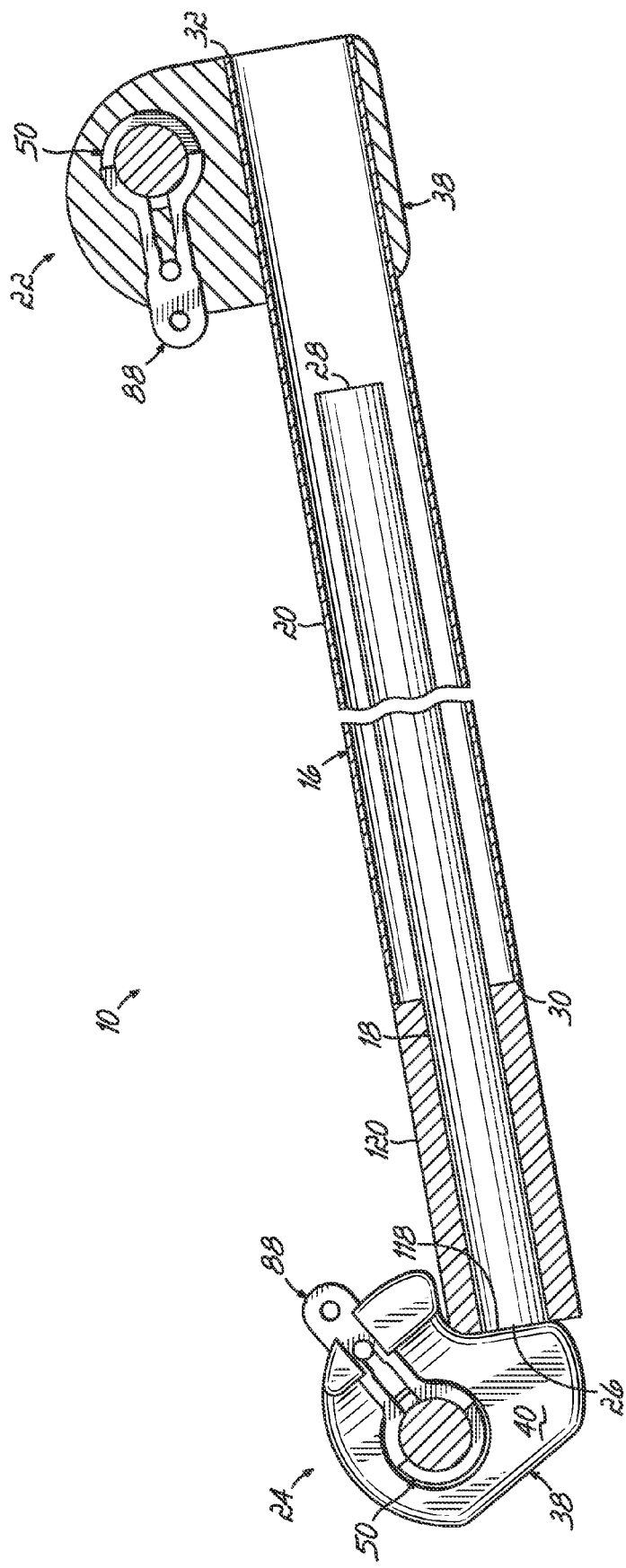
FIG. 12 is a cross-sectional view of an orthodontic device in accordance with another embodiment of the invention.

Orthodontic device 10, as with conventional Herbst devices, may be configured to operate in a Herbst mode even after the jaws 12, 14 begin to move and adapt. In one embodiment, and as shown in FIGS. 10A, 10B and 12, one or more spacers 120 may be readily added to orthodontic device 10 as the jaws 12, 14 move toward proper occlusion. To this end, the orthodontic device 10 may be disassembled and one or more spacers 120 positioned around inner rod 18 so that one end of spacer 120 abuts contact portion 118 on lower connecting device 24 and the other end is spaced from contact portion 118.

The orthodontic device 10 may or may not be removed from the teeth to add the spacer 120. In one approach, the orthodontic device 10 may be designed such that when a patient opens his or her mouth, thereby separating the jaws 12, 14 to substantially the fullest extent, the second end 28 of the inner rod 18 is no longer located within the outer sleeve 20. The inner rod 18 may then be rotated and the spacer 120 placed over the inner rod 18. The patient then opens his mouth to substantially the fullest extent again and the second end 28 of the inner rod is reinserted into the first end 30 of the outer sleeve 20. In this way, the orthodontic device 10 does not have to be removed from the patient to make the necessary adjustments to the orthodontic device 10. It should be recognized, however, that because the connecting devices 22, 24 may be quickly and conveniently removed/coupled to their respective connecting members 50, the spacer(s) 120 may be added by removing the orthodontic device 10 from the patient, disassembling the orthodontic device 10 in a manner described above, adding spacer 120 to inner rod 18, reassembling the orthodontic device 10, and reinstalling the orthodontic device 10 on the patient.

Although spacer 120 may be configured as a tubular type of spacer that is threaded over inner rod 18, as described above, spacer 120 may alternately be configured as a crimpable type of spacer. To this end, the crimpable spacer may be positioned directly on the inner rod 18 without threading the spacer over the second end 28 of the inner rod 18 and crimped thereto. This allows the spacer 120 to be added to the orthodontic device 10 without any disassembly or removal of the device 10 from the patient's mouth.

For either configuration, spacer 120 has an outer cross dimension, e.g. diameter D, that is greater than the inner cross dimension of the outer sleeve 20, as shown in FIG. 12. In this way, an end of spacer 120 operates as the new hard, fixed stop for the orthodontic device 10 and when the patient attempts to close his or her jaws 12, 14, the outer sleeve 20 slides over the inner rod 18 until the first end 30 of outer sleeve 20 contacts the end of the spacer 120. Thus, as with conventional Herbst devices, orthodontic device 10 allows Herbst therapy to be continued even after initial physiological adaptation of the jaws 12, 14.

As mentioned above, the orthodontic device 10 may be selectively activated to operate in a spring-biased mode, as will now be described. As used herein, spring-biased mode means that orthodontic device 10 does not use an impact or a hard, fixed stop to force a patient to close his or her jaws in a proper occlusion, but that a spring applies a biasing force to one of the jaws during at least a portion of the movement of the jaws between an opened and closed position. When the orthodontic device 10 is installed on the maxillary and mandibular jaws 12, 14 and in a closed position, the inner rod 18 is positioned within the outer sleeve 20 but the first end 30 of outer sleeve 20 does not contact the lower connecting device 24, but is spaced from contacting portion 118 on lower connecting device 24. In this way, there is no hard, fixed stop and therefore no Herbst-type treatment of the malocclusion.

Figure 13:
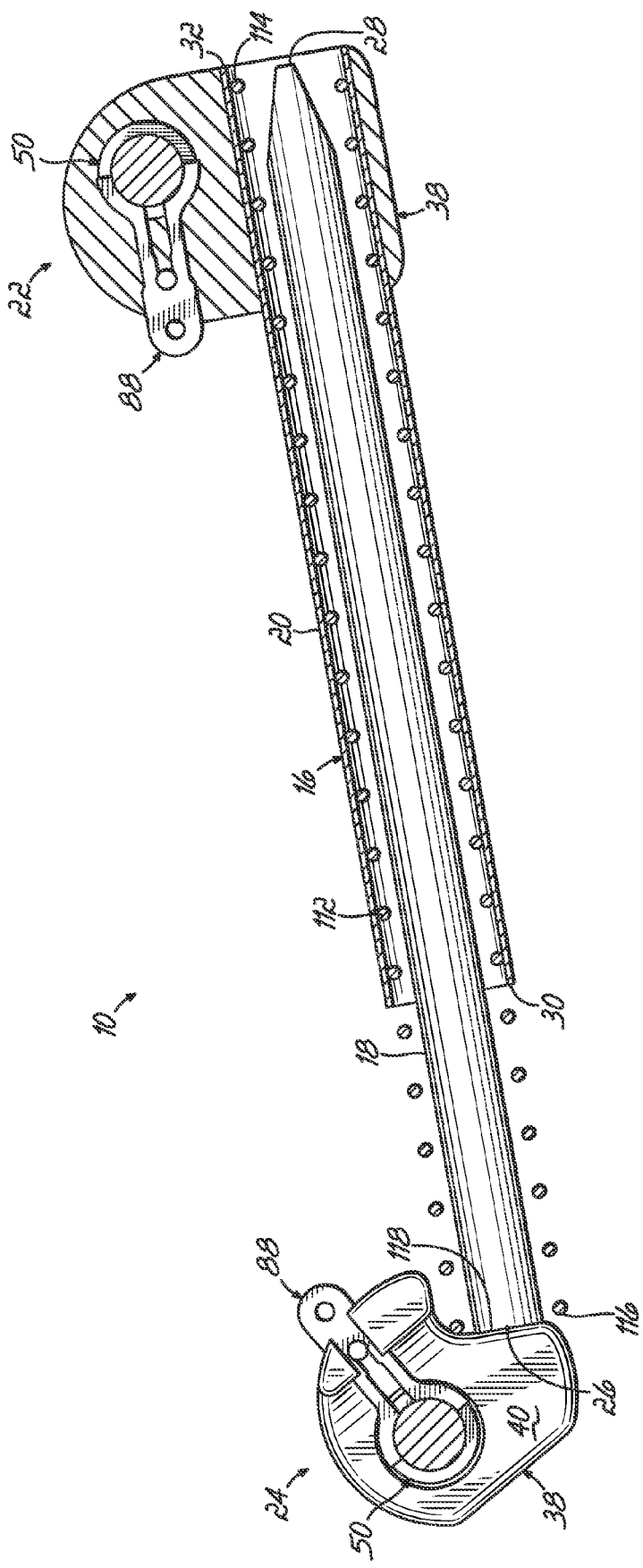
FIG. 13 is a cross-sectional view of an orthodontic device in accordance with another embodiment of the invention.

In this mode, when the jaws 12, 14 are in the closed position, the second end 116 of spring 112 abuts and engages contacting portion 118 on lower connecting device 24, either directly or indirectly as explained below, so that spring 112 is compressed and therefore applies a biasing force to mandibular jaw 14. There are several approaches to activating the spring without also having the first end 30 of the outer sleeve 20 contact the lower connecting device 24. In one embodiment, and as shown in FIG. 13, the spring 112 may be made sufficiently long such that the second end 116 of spring 112 extends beyond the first end 30 of outer sleeve 20. In this way, when the orthodontic device 10 is assembled, either while in the mouth of the patient or when removed from the mouth of a patient, the second end 116 of spring 112 contacts the lower connecting device 24 before the first end 30 of the outer sleeve 20. Those of ordinary skill in the art will recognize that instead of making spring 112 sufficiently long so that second end 116 extends beyond first end 30 of outer sleeve, the first end 114 of spring 112 may be coupled to outer sleeve 20 at a suitable location between the first and second ends 30, 32 of outer sleeve 20 such that the second end 116 extends beyond first end 30 of outer sleeve 20.

For this embodiment, the amount of spring biasing may be determined at least in part by the length of the spring 112 that extends beyond the first end 30 of outer sleeve 20. For instance, the spring 112 may be long enough such that spring 112 is compressed not only when the jaws 12, 14 are closed but also when the jaws 12, 14 are open. In this case, spring 112 applies a biasing force to mandibular jaw 14 as the jaws 12, 14 move between the opened and closed positions. In other words, the second end 116 of spring 112 is in contact with contacting portion 118 on lower connecting device 24 during the entire movement of the jaws 12, 14 between the opened and closed positions.

Alternatively, the spring 112 may be configured such that the spring 112 applies a biasing force to mandibular jaw 14 when the jaws 12, 14 are closed and during a portion of the movement of the jaws 12, 14 between the opened and closed positions. In this case, the second end 116 of spring 112 would initially engage contacting portion 118 on lower connecting device 24, but as the jaws 12, 14 open, the second end 116 would lose contact with lower connecting device 24 and a biasing force would no longer be imposed on the lower connecting device 24 and mandibular jaw 14.

The orthodontic device 10 may be converted between a Herbst mode of operation and a spring-biased mode of operation, as described above, by disassembling the orthodontic device 10 and adding a suitable spring 112 for the desired amount of spring biasing, wherein the amount of biasing may be determined by the length of the spring 112 extending beyond the end 30 of the outer sleeve 20 as explained above. To convert the orthodontic device 10 from a spring-biased mode to a Herbst mode, the device 10 may be disassembled and the spring 112 removed from the orthodontic device 10.

Figure 14:
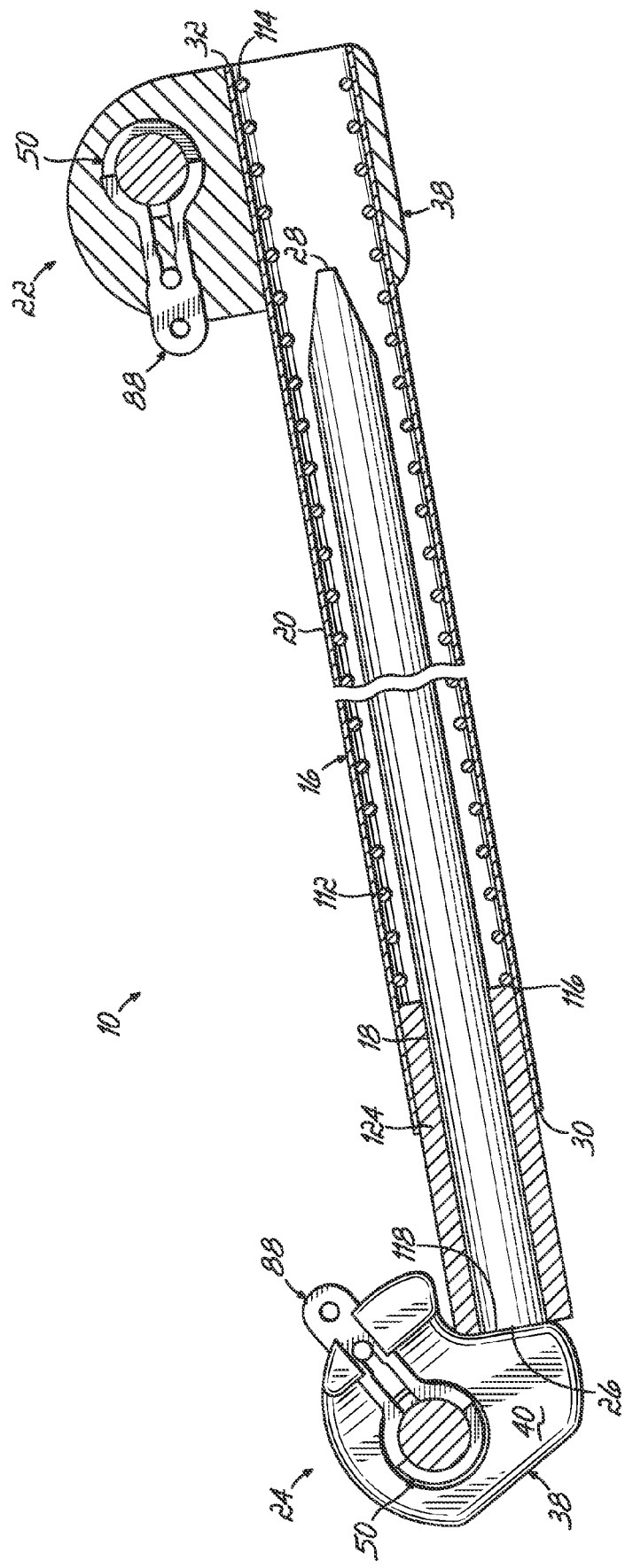
FIG. 14 is a cross-sectional view of an orthodontic device in accordance with another embodiment of the invention.

In another embodiment for activating the spring 112 without also having the first end 30 of the outer sleeve 20 contact the lower connecting device 24, thus operating in a spring-biased mode, is to add one or more spacers 124 onto orthodontic device 10. To this end, and as illustrated in FIGS. 10A, 10B and 14, the orthodontic device 10 may be disassembled and spacer 124 positioned around inner rod 18 so that one end of spacer 124 abuts contact portion 118 on lower connecting device 24. As with the Herbst mode, the addition of spacer 124 to orthodontic device 10 may be accomplished while the device 10 is in a patient's mouth or while removed from the patient's mouth, and in a manner similar to that discussed above. In any event, spacer 124 has an outer cross dimension, e.g. diameter D, that is less than the inner cross dimension of the outer sleeve 20 but greater than the inner cross dimension of the spring 112. Thus, as the patient closes his or her jaws 12, 14, the outer sleeve 20 slides over inner rod 18 and spacer 124 so that the second end 116 of spring 112 contacts an end of spacer 124 thereby compressing spring 112 and applying a biasing force to mandibular jaw 14. In this way, spring 112 does not extend beyond the first end 30 of outer sleeve 20 but is always contained within outer sleeve 20.

For this embodiment, the amount of spring biasing may be determined at least in part by the length of spacer(s) 124 and/or the length of spring 112. For instance, if the spacer 124 is long enough, then spring 112 will be compressed not only when the jaws 12, 14 are in the closed position but also when the jaws 12, 14 are in the open position. In this case, spring 112 applies a biasing force to mandibular jaw 14 as the jaws 12, 14 move between the opened and closed positions. In other words, the second end 116 of spring 112 is in contact with the end of spacer 124 during the entire movement of the jaws 12, 14 between the opened and closed positions.

Alternatively, the spacer 124 may be configured such that the spring 112 applies a force to mandibular jaw 14 when the jaws 12, 14 are closed and during a portion of the movement of jaws 12, 14 between the opened and closed positions. In this case, the second end 116 of spring 112 would initially engage the end of spacer 124 but as the jaws 12, 14 open, the second end 116 would lose contact with spacer 124 and a force would no longer be imposed on the mandibular jaw 14.

For this embodiment, the orthodontic device 10 may be converted between a Herbst mode of operation and a spring-biased mode of operation by disassembling the device 10 and adding a suitable spacer 124 for the desired amount of spring biasing. As those of ordinary skill in the art will recognize, because spring 112 is always contained within outer sleeve 20, the spring 112 may be positioned on the orthodontic device 10 even when operating in a Herbst mode. Thus, when converting between a Herbst mode and a spring-biased mode, only the spacer 124 must be added to the orthodontic device 10. To convert the orthodontic device 10 from a spring-biased mode to a Herbst mode, the orthodontic device 10 may be disassembled and the spacer 124 removed from the device.

Figure 15:
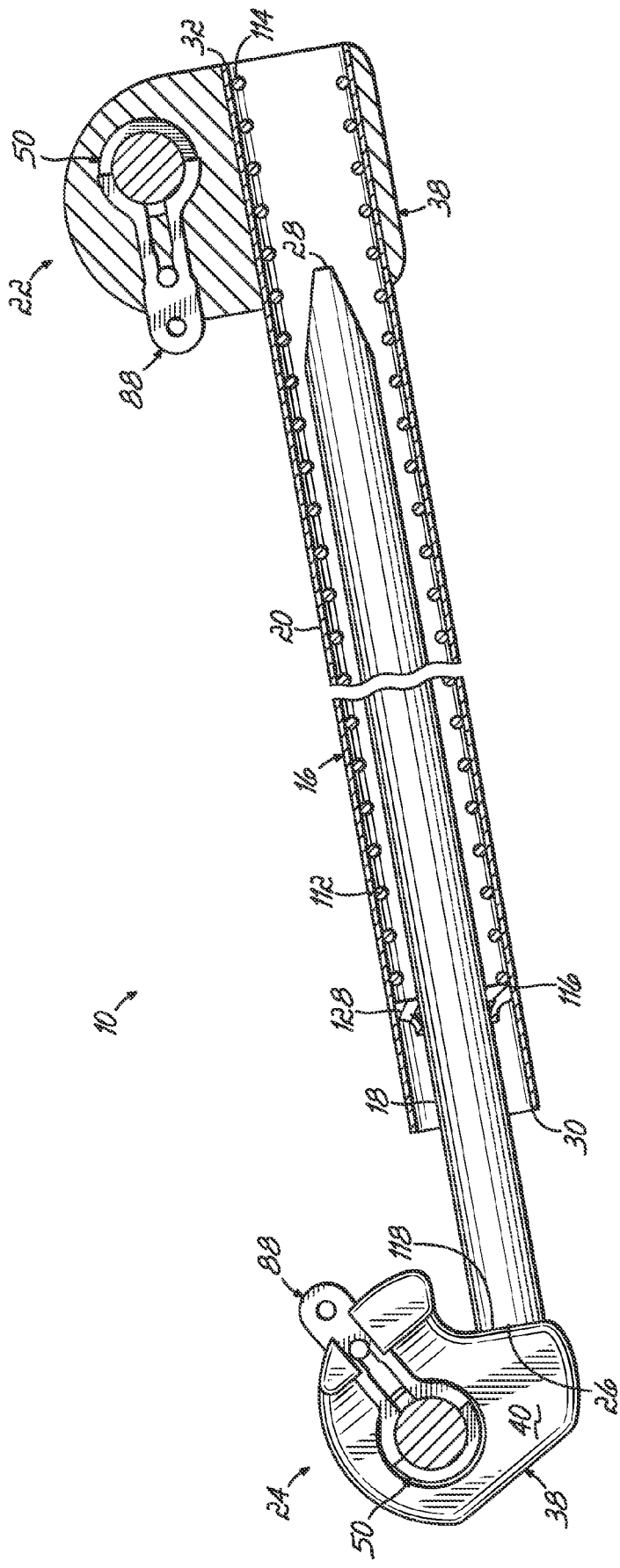
FIG. 15 is a cross-sectional view of an orthodontic device in accordance with another embodiment of the invention.

In another embodiment, and as shown in FIG. 15, instead of using a spacer 124 as shown and described above, wherein one end of spacer 124 engages contact portion 118 on lower connecting device 24 and the other end contacts the second end 116 of spring 112 (at least for a portion of the movement of jaws 12, 14 between the opened and closed positions), a shim or crimpable stop 128 may be utilized. In this embodiment, the crimpable stop 128 may be selectively positioned along the inner rod 18 in order to provide the desired amount of spring biasing for the orthodontic device 10. To this end, the orthodontic device 10 may be disassembled and crimpable stop 128 applied to the inner rod 18. Unlike spacers 120, 124, crimpable stop 128 is not capable of moving relative to inner rod 18 but is rigidly affixed thereto.

Crimpable stop 128 has an outer cross dimension, e.g. diameter, that is less than the inner cross dimension of the outer sleeve 20 but greater than the inner cross dimension of the spring 112. Thus, as the patient closes his or her jaws 12, 14, the outer sleeve 20 slides over inner rod 18 and crimpable stop 128 so that the second end 116 of spring 112 contacts the crimpable sleeve 128 thereby compressing spring 112 and applying a force to mandibular jaw 14. In this embodiment, the amount of spring biasing may be determined by the positioning of crimpable stop 128 along inner rod 18. For instance, if the crimpable stop 128 is positioned sufficiently toward the second end 28 of inner rod 18, then spring 112 will be compressed not only when the jaws 12, 14 are in the closed position but also when the jaws 12, 14 are in the open position. In this case, spring 112 applies a force to mandibular jaw 14 during the entire movement of the jaws 12, 14 between the opened and closed positions. In other words, the second end 116 of spring 112 is in contact with the crimpable stop 128 during the entire movement of the jaws 12, 14 between the open and closed positions.

Alternatively, the crimpable stop 128 may be positioned sufficiently toward the first end 26 of inner rod 18 such that the spring 112 applies a force to mandibular jaw 14 when the jaws 12, 14 are closed and during a portion of the movement of jaws 12, 14 between the opened and closed positions. In this case, the second end 116 of spring 112 would initially engage the crimpable stop 128 but as the jaws 12, 14 open, the second end 116 would lose contact with crimpable stop 128 and a biasing force would no longer be imposed on the mandibular jaw 14.

For this embodiment, the orthodontic device 10 may be converted between a Herbst mode of operation and a spring-biased mode of operation by disassembling the device 10 and adding a crimpable stop 128 for the desired amount of spring biasing. As those of ordinary skill in the art will recognize, because spring 112 may always be contained within outer sleeve 20, the spring 112 may be positioned on the orthodontic device 10 even when operating the device in a Herbst mode. Thus, when converting between a Herbst mode and a spring-biased mode, only the crimpable stop 128 must be added to the orthodontic device 10 and properly positioned on the inner rod 18. To convert the orthodontic device 10 from a spring-biased mode to a Herbst mode, the orthodontic device 10 may be disassembled and the crimpable stop 128 removed from the inner rod 18 as is known in the art. As those of ordinary skill in the art will recognize, to add or remove the crimpable stop 128 to orthodontic device 10, the device may not require disassembly but may only require the patient to open his or her mouth a sufficient distance so as to apply or remove crimpable stop 128 to/from inner rod 18.

In an advantageous aspect of this embodiment, the spring 112 may be shorter than the outer sleeve 20 such that the spring 112 and the crimpable stop 128 (but not crimped so as to be fixed to inner rod 18) may be pre-loaded onto orthodontic device 10 and orthodontic device 10 still be capable of operating in a Herbst mode. In this way, to convert from the Herbst mode to a spring-biased mode, nothing has to be added onto device 10, as was discussed above, but the crimpable stop 128 must only be crimped or fixed to the inner rod 18 at the desired location. This may be done without disassembling the orthodontic device 10 thereby further simplifying the conversion between the Herbst mode and spring-biased mode.

In addition to exclusively operating in a Herbst mode or a spring-biased mode, the orthodontic device 10 may further operate in a mixed mode, using both a hard, fixed stop to force a patient to close his or her jaws in a proper occlusion and spring biasing to urge the mandibular jaw or teeth to the proper occlusion. In the mixed mode, when the orthodontic device 10 is installed and the maxillary and mandibular jaws 12, 14 are in a closed position, the inner rod 18 is positioned within the outer sleeve 20 and the first end 30 of outer sleeve 20 engages contact portion 118 on the lower connecting device 24 or the end of a spacer 120 as described above. In addition, when the jaws 12, 14 are in the closed position, the second end 116 of spring 112 either engages: i) contact portion 118; ii) an end of spacer 120; iii) the end of spacer 124; or iv) the crimpable stop 128, depending on the particular embodiment of the orthodontic device 10 used for treatment. In the mixed mode, the amount of spring biasing may made be adjusted in accordance with the particular embodiment and the description provided above for that embodiment. Thus, the mixed mode orthodontic device 10 may be configured to apply a spring biased force to mandibular jaw 14 for the entire movement of the jaws 12, 14 between the opened and closed positions or alternately for a portion of the movement of the jaws 12, 14 between the opened and closed positions. The mixed mode of operation may provide a synergistic effect that proves to be advantageous to the treatment of malocclusions.

Figure 16B:
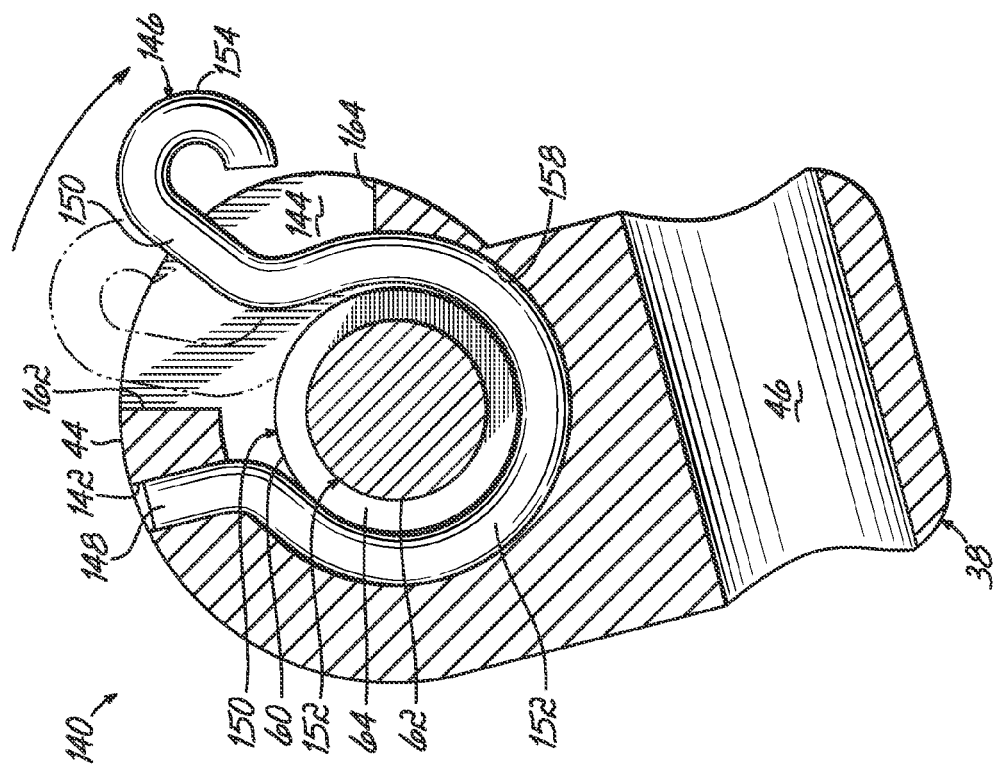
FIG. 16B is a cross-sectional view of the lower connecting device shown in FIG. 16A with the blocking member in the opened position.
Figure 16A:
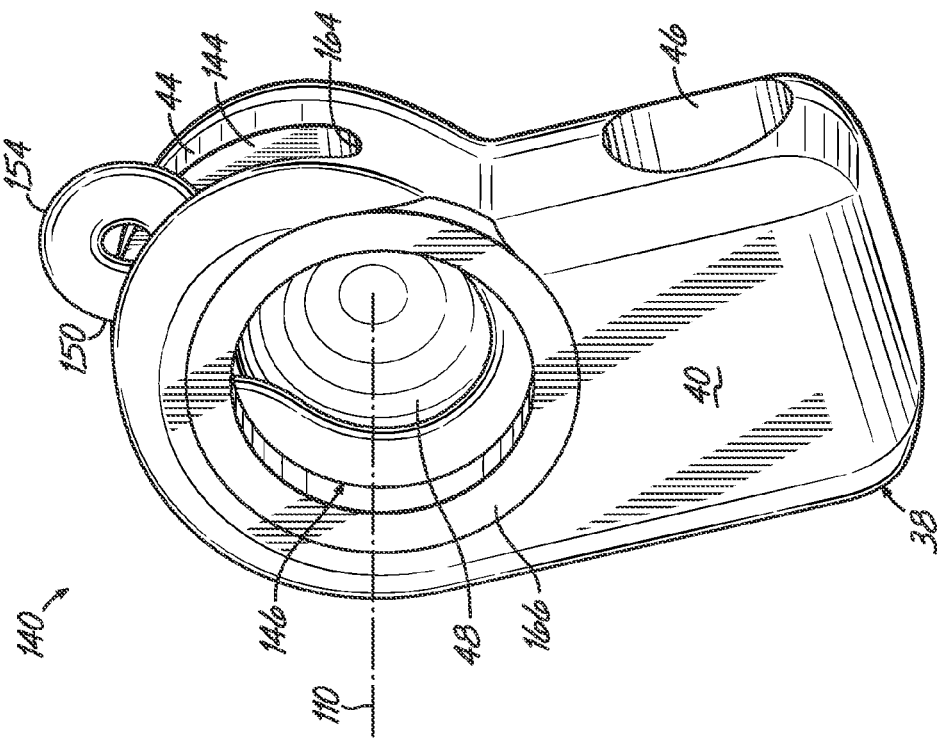
FIG. 16A is a perspective view of a lower connecting device in accordance with another embodiment of the invention.
Figure 16C:
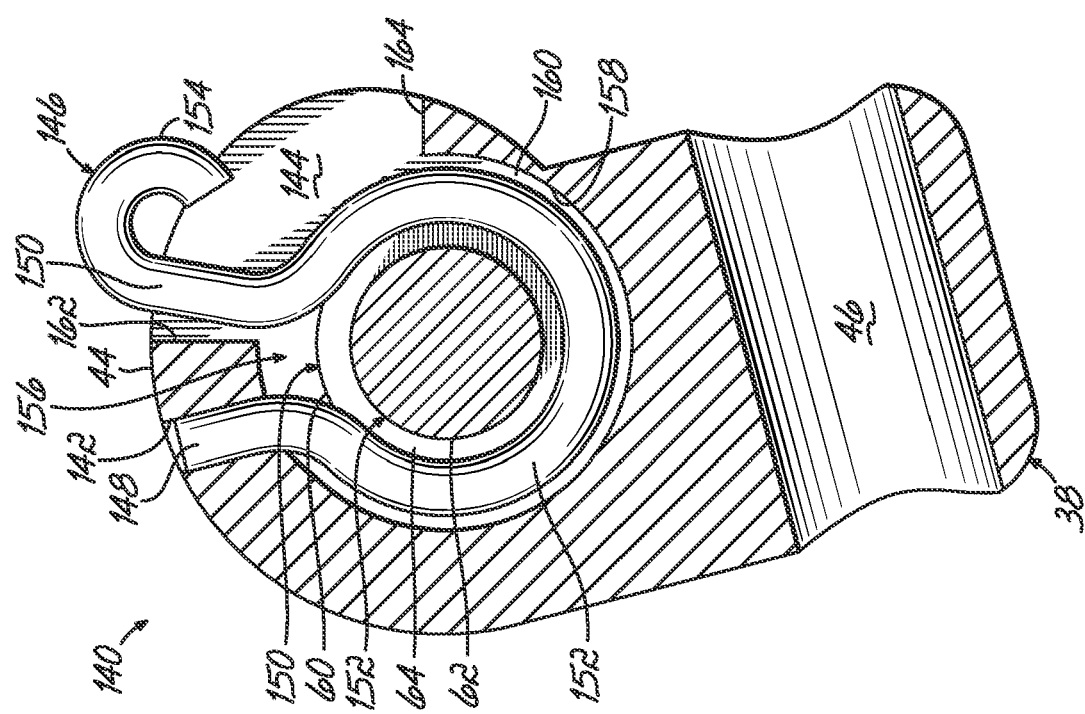
FIG. 16C is a view of the lower connecting device shown in FIG. 16B with the blocking member in the closed position.

FIGS. 16A-16C, in which like reference numerals refer to like features in FIGS. 1-15, illustrate a connecting device in accordance with an alternate embodiment of the invention. Like the previous connecting device, this connecting device may be configured as a unitary assembly, devoid of screws, bayonet pins, auxiliary wires or other detached parts, which may be selectively coupled to or removed from the upper and lower dental arches in a quick and convenient manner. For illustration purposes, the aspects of this embodiment will be described using a lower connecting device 140. More particularly, as the lower connecting device 140 is similar to lower connecting device 24 shown and described above, only the differences in the connecting devices 24, 140 will be discussed in significant detail. As noted below, the primary difference in connecting devices 24, 140 is the configuration of the blocking member that facilitates securing an orthodontic device, such as the multi-mode orthodontic device discussed above, to connecting member 50.

As shown in FIG. 16A, the tooth-facing surface 40 of the lower connecting device 140 includes a receptacle 48 adapted to receive the ball portion 60 of connecting member 50 in a manner similar to that described above. The side surface 44 of connecting device 140 includes a generally cylindrical aperture 142 that extends from the side surface 44 and intersects the receptacle 48 in tooth-facing surface 40. The side surface 44 of connecting device 140 further includes a slot 144 that extends along side surface 44. Slot 144 also has a depth that extends from side surface 44 and intersects the receptacle 48.

As shown in FIGS. 16B and 16C, connecting device 140 further includes a blocking member, represented by resilient spring clip 146, that is configured to selectively retain/release an orthodontic device from connecting member 50. To this end, spring clip 146 includes a first end portion 148, second end portion 150 and an intermediate portion 152. The first end portion 148 is fixedly secured within the aperture 142 in connecting device 140. The second end portion 150 is positioned in slot 144 and includes a partial hook or loop 154 that facilitates movement of the second end portion 150, such as with a suitable tool (not shown), along slot 144, as will be discussed in more detail below. The intermediate portion 152 of spring clip 146 has a generally circular shape. The spring clip 146 defines an opening or gap 156 between the first and second end portions 148, 150 that permits relative movement of the ends relative to each other for purposes that will now be discussed.

As shown in FIGS. 16B and 16C, when the spring clip 146 is mounted within the connecting device 140, the second end portion 150 is movable between a closed position and an opened position along slot 144. In the closed position (FIG. 16C), the spring clip 146 may be in an unbiased state and the intermediate portion 152 has an inner cross dimension that is smaller than the cross dimension of ball portion 60 of connecting member 50 at shoulder 64, but larger than the cross dimension of neck portion 62. In addition, when spring clip 146 is in the closed position, the intermediate portion 152 has an outer cross dimension less than the cross dimension of a bore 158 of receptacle 48 in which spring clip 146 is mounted. This difference in cross dimensions defines a slight gap 160 between the spring clip 146 and bore 158 that allows the spring clip 146 to expand outward as the second end portion 150 is moved toward the opened position. Furthermore, in the closed position the second end portion 150 of spring clip 146 may be adjacent a first end 162 of slot 144.

In the opened position (FIG. 16B), however, the spring clip 146 is in a biased state, such as by application of a sufficient force by a tool (not shown) engaged with hook 154, such that the inner cross dimension of the intermediate portion 152 is larger than the cross dimension of the ball portion 60. Thus, the ball portion 60 may be moved past the spring clip 146, either toward or away from receptacle 48, when the spring clip 146 is in the opened position. In the opened position, the spring clip 146 has expanded outward to fill or at least reduce the size of gap 160 between the spring clip 146 and the bore 158 of receptacle 48. In the opened position, the second end portion 150 may be adjacent a second end 164 of slot 144.

The spring clip 146 and receptacle 48 of connecting device 140 cooperate to couple connecting device 140 to connecting member 50, which is coupled to mandibular jaw 14. To this end, the spring clip 146 may be moved to the opened position by moving the second end portion 150 toward the second end 164 of slot 144 so as to expand intermediate portion 52 outwardly. The connecting device 140 may then be positioned over connecting member 50 such that ball portion 60 is received in receptacle 48 as connecting member 140 is moved toward the teeth. Once the ball portion 60 is located in receptacle 48, the spring clip 146 may be released or moved to the closed position by locating the second end portion 150 toward the first end 162 of slot 144. For example, this movement may be due to the release of the force applied by the tool such that the resiliency of the spring clip 146 causes the movement toward the closed position. As shown in FIG. 16C, the intermediate portion 152 of the spring clip 146 extends about neck portion 62 and engages against shoulder 164 so that connecting device 140 is securely coupled to connecting member 50.

As shown in FIG. 16A, connecting device 140 may also include a retaining ring 166 that engages a bore adjacent tooth-facing surface 40 in an interference fit or other secured manner known in the art. The retaining ring 166 permits the insertion of the spring clip 146 into position within connecting device 140 via tooth-facing surface 40 during assembly and further prevents undesired movement of the spring clip 146 away from receptacle 48 to maintain its position relative thereto. For example, the retaining ring 166 may prevent canting of the spring clip 146 within connecting device 140 as well as other undesired movements of the spring clip.

As in the previous embodiments, the spring clip 146 prevents undesired movement of the connecting device 140 away from the connecting member 50 along axis 110, but yet permits rotation of the connecting device 140, and thus an orthodontic device coupled thereto, around axis 110. In addition, connecting device 140 may be selectively coupled to or removed from connecting member 50 by movement of the spring clip 146 between the opened and closed positions. This allows an orthodontic device to be installed and removed from the teeth in a quick and convenient manner. Furthermore, although not shown, those of ordinary skill in the art will recognize that an upper connecting member similar to connecting device 140 may be used to mount an orthodontic device to the teeth. Any modifications between the upper and lower connecting devices for operation of the orthodontic device are readily recognized by those of ordinary skill in the art. Moreover, connecting device 140 may be used in a wide variety of orthodontic devices where a connection between the device and the upper and/or lower arches is desired.

Figure 17A:
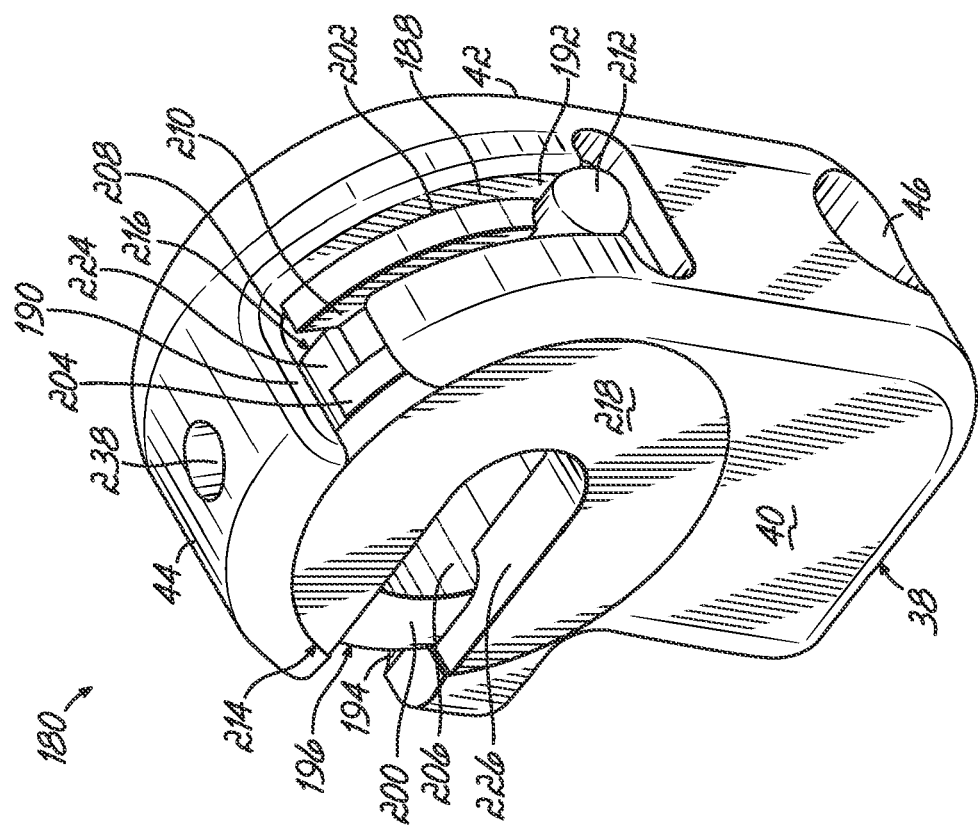
FIG. 17A is a perspective view of a lower connecting device in accordance with another embodiment of the invention.
Figure 17B:
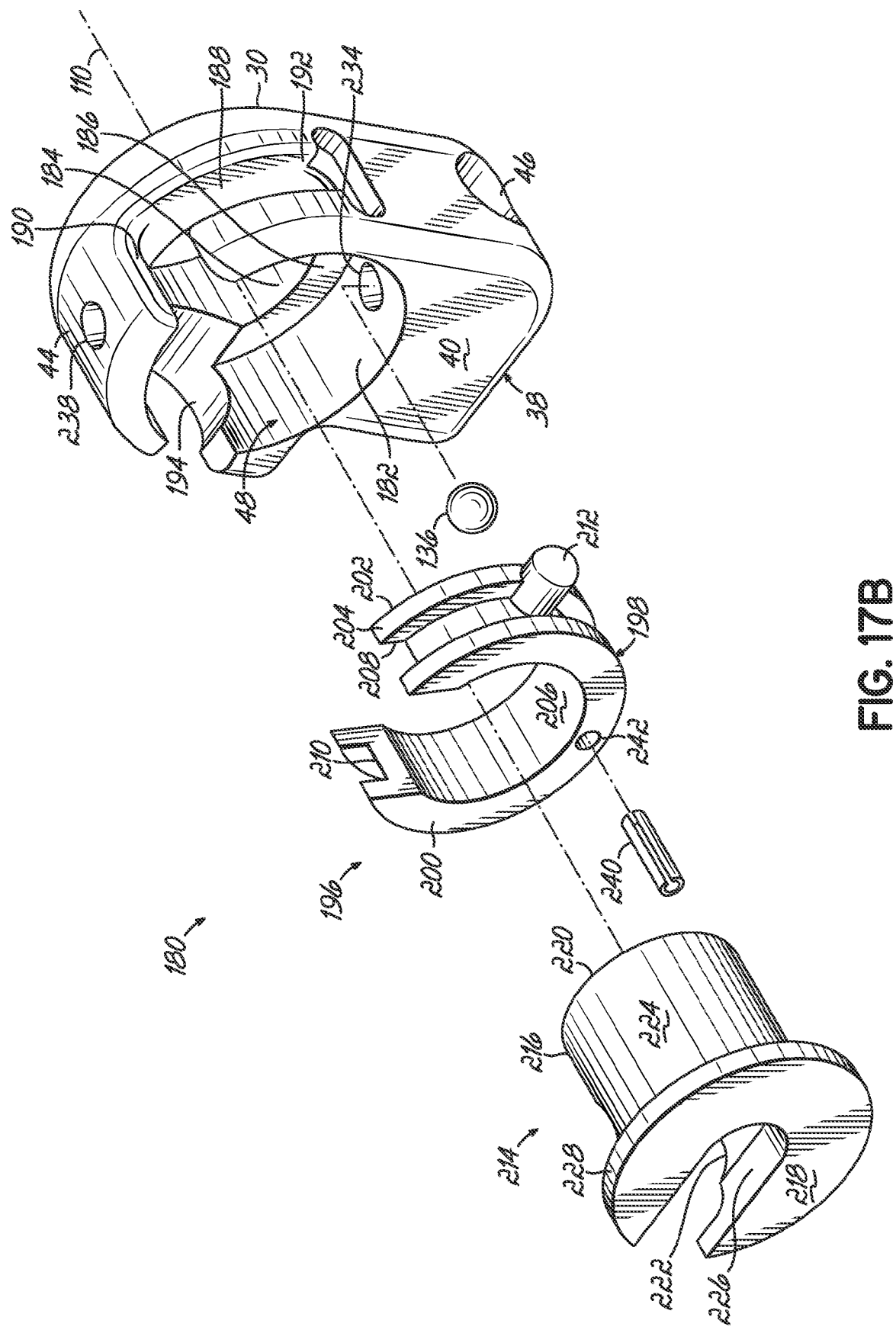
FIG. 17B is a disassembled perspective view of the lower connecting device shown in FIG. 17A.

FIGS. 17A-17D, in which like reference numerals refer to like features in FIGS. 1-15, illustrate a connecting device in accordance with an alternate embodiment of the invention. Like the previous connecting devices, this connecting device may be configured as a unitary assembly, devoid of screws, bayonet pins, auxiliary wires or other detached parts, which may be selectively coupled to or removed from the upper and lower dental arches in a quick and convenient manner. For illustration purposes, the aspects of this embodiment will be described using a lower connecting device 180. As shown in FIGS. 17A and 17B, the tooth-facing surface 40 of lower connecting device 180 includes a receptacle 48 adapted to receive the ball portion 60 of connecting member 50. The receptacle 48 is configured as a bore having a first bore portion 182 and a second bore portion 184 that collectively extend from tooth-facing surface 40 to buccal surface 42. The cross dimension of the second bore portion 184 is smaller than the cross dimension of the first bore portion 182 to define shoulder 186 therebetween.

The side surface 44 of connecting device 180 includes a J-shaped slot 188 that extends along side surface 44 between first and second ends 190, 192 and which is open to surface 40 at first end 190. Slot 188 has a depth that extends from side surface 44 and intersects receptacle 48, such as along first bore portion 182. Side surface 44 further includes a bore 194 that has a depth that extends from side surface 44 and intersects receptacle 48. The bore 194 is also open to tooth-facing surface 40 of connecting device 180. In contrast to previous embodiments, the ball portion 60 of connecting member 50 is not inserted into receptacle 48 via tooth-facing surface 40, but instead is inserted into receptacle 48 via bore 194, as discussed in more detail below.

Figure 17D:
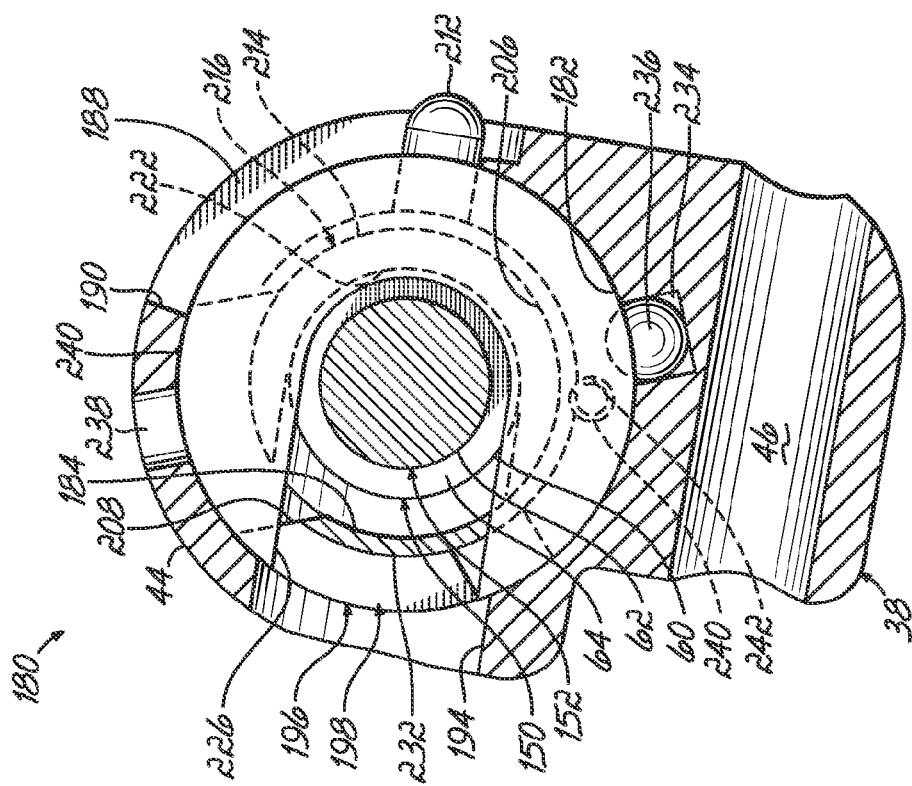
FIG. 17D is a cross-sectional view of the lower connecting device shown in FIG. 17A with the blocking member in the closed position.
Figure 17C:
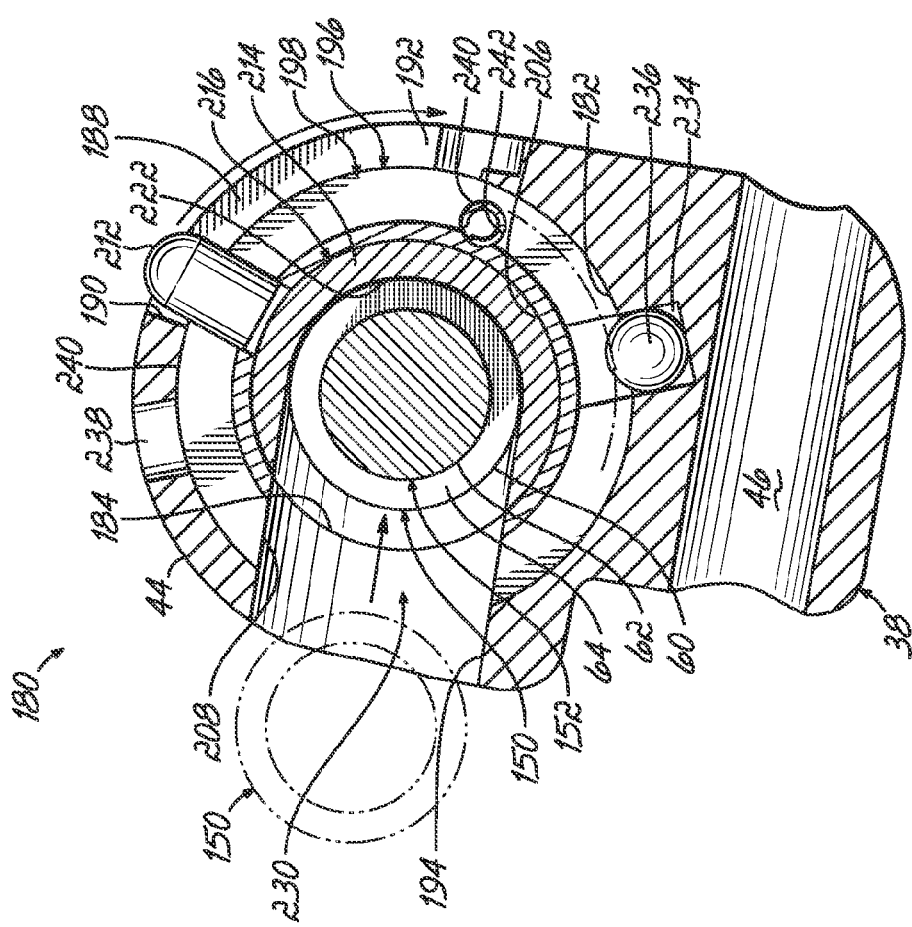
FIG. 17C is a cross-sectional view of the lower connecting device shown in FIG. 17A with the blocking member in the opened position.

As shown in FIGS. 17B-17D, connecting device 180 further includes a blocking member, represented by a rotatable drum 196, that is configured to selectively retain/release an orthodontic device from connecting member 50. To this end, rotatable drum 196 includes a disc-shaped body 198 having a first surface 200, a second surface 202 and a side surface 204 connecting the first and second surfaces 200, 202. The body 198 further includes a central aperture 206 extending therethrough between the first and second surfaces 200, 202. The central aperture 206 is open to side surface 204 along a cutout portion 208 that gives the body 198 a C-shaped configuration. The cutout portion 208 has a cross dimension substantially the same as the cross dimension of the bore 194 in connecting device 180 so as to accommodate the ball portion 60 of connecting member 50. Moreover, the side surface 204 of drum 196 includes a generally rectangular channel 210 formed therein. A pin member 212 is positioned at least in part in the channel 210 and projects outwardly therefrom.

As shown in FIGS. 17A and 17B, the connecting device 180 further includes a retaining member 214 having a generally cylindrical shaft portion 216 and a head portion 218. The shaft portion 216 has a cross dimension substantially equal to the cross dimension of the second bore portion 184 of connecting device 180 and is adapted to be received therein. The terminating end 220 of shaft portion 216 is solid and is substantially flush with buccal surface 42 when positioned in receptacle 48. The cross dimension of shaft portion 216 is also substantially equal to or less than the cross dimension of the central aperture 206 of drum 196 so that drum 196 is capable of rotating relative to shaft portion 216 when mounted thereon. Shaft portion 216 further includes a cavity 222 therein that is open to an outer side surface 224 of shaft portion 216. Cavity 222 is adapted to receive ball portion 60 of connecting member 50 therein.

The head portion 218 of retaining member 214 is generally cylindrical and has a cross dimension substantially equal to the cross dimension of the first bore portion 182 of receptacle 48 and is adapted to be received therein. Head portion 218 includes a U-shaped slot 226 open to the outer side surface 228 of the head portion 218 and intersecting the cavity 222 in shaft portion 216. The cross dimension of the U-shaped slot 226 is less than the cross dimension of the ball portion 60 of connecting member 50 adjacent shoulder 64 but larger than the cross dimension of the neck portion 62. The retaining member 214 may be securely coupled to connecting device 180 so that the cavity 222 in shaft portion 216 and U-shaped slot 226 in head portion 218 aligns with the cylindrical bore 194 in the side surface 44 of connecting device 180. For example, the retaining member 214 may be coupled through an interference fit, adhesives or other methods known to those of ordinary skill in the art.

As shown in FIGS. 17C and 17D, when the retaining member 214 and drum 196 are mounted in connecting device 180, the drum 196 is rotatable between a closed position and an open position by moving pin member 212 along slot 188. In the opened position, the pin member 212 is adjacent the first end 190 of slot 188 and the cutout portion 208 of drum 196 is aligned with the cylindrical bore 194 in connecting device 180 and the cavity 222 and U-shaped slot 226 in the retaining member 214. As shown in FIG. 17C, this provides an open pathway 230 for inserting the ball portion 60 of connecting member 50 into receptacle 48, and more particularly, into the cavity 222 of retaining member 214.

In the closed position, the pin member 212 has been moved along slot 188 so as to be adjacent second end 192 thereby rotating drum 196 relative to retaining member 214. In the closed position, the cutout portion 208 no longer aligns with the cylindrical bore 194 in connecting device 180 and the cavity 222 and U-shaped slot 226 in the retaining member 214. Instead, a blocking portion 232 of drum 196 closes off the pathway 230 and prevents movement of the ball portion 60 of connecting member 50 along pathway 230. Moreover, as noted above, the U-shaped slot 226 is sized to prevent the ball portion 60 from moving away from receptacle 48 along axis 110.

As in the embodiment shown in FIGS. 1-15, connecting device 180 may also include a mechanism to limit the movement of the drum 196 between the opened and closed positions. As shown in FIG. 17B, the connecting device 180 includes a blind bore 234 formed along an inner surface of first bore portion 182 and adapted to receive a ball 236 therein in a press fit manner. Those of ordinary skill in the art will recognize other ways to secure ball 236 in blind bore 234. Ball 236 has a portion that projects into first bore portion 182. The blind bore 234 may, for example, be formed in the inner surface of first bore portion 182 by inserting a suitable tool through an aperture 238 in side surface 44 of connecting member 180. When the drum 196 is mounted in the connecting member 180, the projecting portion of the ball 236 rides in the channel 210 of drum 196 with limited resistance to rotation. To provide resistance to rotation of drum 196, the drum 196 includes a C-shaped spring pin 240 positioned in a bore 242 adjacent side surface 204 and extending between the first and second surfaces 200, 202. The spring pin 240 includes a portion that projects into channel 210.

As shown in FIGS. 17C and 17D, the ball 236 and spring pin 240 cooperate to provide resistance to rotation of drum 196 between the opened and closed positions. As the drum 196 is rotated from the opened position toward the closed position, the spring pin 240 engages the ball 236. A sufficient force must then be applied so as to deform the spring pin 240 and allow the drum 196 to rotate so that the spring pin 240 moves past the ball 236 to the closed position. To move the drum to the opened position, a sufficient force must again be applied to deform the spring pin 240 and allow the drum to rotate so that spring pin 240 moves past the ball 236 to the opened position.

The retaining member 214, drum 196 and receptacle 48 of connecting device 180 cooperate to couple connecting device 180 to connecting member 50, which is coupled to mandibular jaw 14. To this end, the drum 196 may be rotated to the opened position by moving the pin member 212 toward the first end 190 of slot 188 so that cutout portion 208 is aligned with cylindrical bore 194 in connecting device 180 and cavity 222 and U-shaped slot 226 in retaining member 214 so that pathway 230 is open. The connecting device 180 may then positioned relative to connecting member 50 such that ball portion 60 is received in receptacle 48 as connecting device 180 is moved in a direction generally parallel to (i.e., mesially-distally) the teeth. Once the ball portion 60 is located in receptacle 48, the drum 196 may be rotated to the closed position by moving the pin member 212 toward the second end 192 of slot 188. A sufficient force must be applied so as to overcome the resistance between the spring pin 240 and the ball 236. When in the closed position, blocking portion 232 then covers pathway 230 to securely couple the connecting device 180 to the connecting member 50.

The drum 196 and retaining member 214 prevent undesired movement of the connecting device 180 away from the connecting member 50 along and transverse to axis 110, but yet permits rotation of the connecting device 180, and thus an orthodontic device coupled thereto, around axis 110. In addition, connecting device 180 may be selectively coupled to or removed from connecting member 50 by movement of the drum 196 between the opened and closed positions. This allows an orthodontic device to be installed and removed from the teeth in a quick and convenient manner. Furthermore, although not shown, those of ordinary skill in the art will recognize that an upper connecting member similar to connecting device 180 may be used to mount an orthodontic device to the teeth. Any modifications between the upper and lower connecting devices for operation of the orthodontic device are readily recognized by those of ordinary skill in the art. Moreover, connecting device 180 may be used in a wide variety of orthodontic devices where a connection between the device and the upper and/or lower arches is desired.

While the invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope or spirit of applicants' general inventive concept.

What is claimed is:

1. An orthodontic treatment method for repositioning a mandibular jaw relative to a maxillary jaw, comprising:
   securing inner and outer telescoping members of an orthodontic device between the mandibular jaw and the maxillary jaw;
   configuring the inner and outer telescoping members of the orthodontic device to operate in a Herbst operating mode to reposition the mandibular jaw relative to the maxillary jaw, wherein the Herbst operating mode lacks a biasing force from a biasing member and includes contacting engagement between the inner telescoping member and a fixed stop or between the outer telescoping member and the fixed stop; and
   activating a biasing member carried by the telescoping members of the orthodontic device to convert the orthodontic device from the Herbst operating mode to a second operating mode in which the active biasing member applies a biasing force directed to reposition the mandibular jaw relative to the maxillary jaw.

2. The orthodontic treatment method of claim 1 wherein the second operating mode is a spring-biased mode and the biasing force is a spring bias.

3. The orthodontic treatment method of claim 1 wherein the second operating mode is a mixed operating mode capable of simultaneously operating in both the Herbst operating mode and a spring-biased mode.

4. The orthodontic treatment method of claim 1 wherein activating the biasing member includes activating a compressing spring with coils, the method further comprising:
   crimping a crimpable stop on the inner telescoping member that abuts the coils of the compression spring for causing compression of the coils as the mandibular jaw moves relative to the maxillary jaw to thereby apply the biasing force.

5. The orthodontic treatment method of claim 1 wherein activating the biasing member includes activating a compression spring with coils, the method further comprising:
   applying a spacer on the inner telescoping member that abuts the coils of the compression spring for causing compression of the coils as the mandibular jaw moves relative to the maxillary jaw and to thereby apply the biasing force.

6. The orthodontic treatment method of claim 5 further comprising positioning the spacer within the outer member during a portion of the relative telescopic movement of the inner and outer members.

7. The orthodontic treatment method of claim 5 further comprising retaining the coil spring within the outer member during the full relative telescopic movement of the inner and outer members.

8. The orthodontic treatment method of claim 5 wherein the step of activating the biasing member further comprises maintaining contact between an end of the coil spring and an end of the spacer during only a portion of the relative telescopic movement of the inner and outer members.

9. The orthodontic treatment method of claim 5 wherein the step of activating the biasing member further comprises maintaining contact between an end of the coil spring and an end of the spacer during the full relative telescopic movement of the inner and outer members.

10. The orthodontic treatment method of claim 1 wherein the contacting engagement includes contacting an end of the outer telescoping member with a connecting device of the orthodontic device to provide the fixed stop for the relative telescopic movement of the inner and outer members.

11. The orthodontic treatment method of claim 10 wherein contacting occurs when the jaws are closed.

12. The orthodontic treatment method of claim 1 wherein the step of operating the inner and outer telescoping members of the orthodontic device in a Herbst operating mode further comprises:
    positioning a spacer on the inner member; and
    contacting an end of the outer member with an end of the spacer to provide the fixed stop for the relative telescopic movement of the inner and outer members.

13. The orthodontic treatment method of claim 1 wherein the step of activating the biasing member further comprises activating the biasing member while the orthodontic device remains coupled to the mandibular and maxillary jaws.

14. The orthodontic treatment method of claim 1 further comprising removing the orthodontic device from the mandibular and maxillary jaws before activating the biasing member.

15. The orthodontic treatment method of claim 1 wherein the step of activating the biasing member further comprises activating the biasing member so that the biasing force acts between the inner and outer members during only a portion of the relative telescopic movement of the inner and outer members.

16. The orthodontic treatment method of claim 1 wherein the step of activating the biasing member further comprises activating the biasing member so that the biasing force acts between the inner and outer members during the full relative telescopic movement of the inner and outer members.

17. The orthodontic treatment method of claim 1 further comprising deactivating the biasing member to revert back to a Herbst operating mode.

18. The orthodontic treatment method of claim 1 further comprising retaining the biasing member in the orthodontic device when operating in a Herbst mode.

* * * * *